(12) United States Patent
Lim

(10) Patent No.: US 10,265,013 B2
(45) Date of Patent: Apr. 23, 2019

(54) SYSTEM AND METHOD FOR SLEEP DISORDER DIAGNOSIS AND TREATMENT

(71) Applicant: SOMNOLOGY, INC., Redwood City, CA (US)

(72) Inventor: Melissa Susann Lim, San Francisco, CA (US)

(73) Assignee: SOMNOLOGY, INC., Redwood City, CA (US)

( * ) Notice: Subject to any disclaimer, the term of this patent is extended or adjusted under 35 U.S.C. 154(b) by 291 days.

(21) Appl. No.: 15/244,999

(22) Filed: Aug. 23, 2016

(65) Prior Publication Data

US 2016/0367184 A1 Dec. 22, 2016

Related U.S. Application Data

(63) Continuation-in-part of application No. 14/020,741, filed on Sep. 6, 2013.

(51) Int. Cl.
*A61B 5/00* (2006.01)
*A61M 21/02* (2006.01)
(Continued)

(52) U.S. Cl.
CPC .......... *A61B 5/4818* (2013.01); *A61B 5/0022* (2013.01); *A61B 5/4815* (2013.01);
(Continued)

(58) Field of Classification Search
None
See application file for complete search history.

(56) References Cited

U.S. PATENT DOCUMENTS

| 4,999,772 A | 3/1991 | Bowman |
| 5,398,682 A | 3/1995 | Lynn |

(Continued)

FOREIGN PATENT DOCUMENTS

| WO | WO/1994/004071 A1 | 3/1994 |
| WO | WO/1995/000001 A1 | 1/1995 |

(Continued)

OTHER PUBLICATIONS

PCT International Search Report and Written Opinion, PCT/US2014/054127, dated Dec. 18, 2014.

(Continued)

*Primary Examiner* — Michael Tomaszewski
(74) *Attorney, Agent, or Firm* — Inventive Law Inc.; Jim H. Salter

(57) ABSTRACT

A system and method for sleep disorder diagnosis and treatment are disclosed. A particular embodiment is configured to: establish a wireless data communication interface between a networked data processor and a sleep metering system, the sleep metering system being worn by a user and including a sensor array, wireless transceiver, and a processor; activate the sleep metering system to begin collection of sensor data from the user based on data signals from the sensor array of the sleep metering system; and detect a sleep-related condition in the user by use of the sleep metering system, the detection of the sleep-related condition including detecting anomalies in breathing patterns of the user by wirelessly receiving a plurality of sets of breathing pattern data from the sleep metering system at a plurality of pre-defined time intervals within a single sleep period, the breathing pattern data corresponding to variations in the degree of the user's chest cavity movement in a series of breaths over a given time interval, the detection of the sleep-related condition further including using the plurality (Continued)

of sets of breathing pattern data to score any detected respiratory effort reduction or exaggeration condition for a level of severity over the plurality of pre-defined time intervals.

20 Claims, 43 Drawing Sheets

(51) Int. Cl.
    *G06F 19/00*     (2018.01)
    *G16H 10/20*     (2018.01)
    *G16H 40/63*     (2018.01)
    *G16H 10/60*     (2018.01)
    *G16H 15/00*     (2018.01)
    *G16H 40/67*     (2018.01)
    *G16H 50/30*     (2018.01)
    *A61B 5/113*     (2006.01)
    *A61B 5/145*     (2006.01)
    *A61M 21/00*     (2006.01)
    *A61B 5/01*     (2006.01)
    *A61B 5/024*     (2006.01)
    *A61B 5/053*     (2006.01)
    *A61B 5/08*     (2006.01)
    *A61B 5/087*     (2006.01)
    *A61B 5/11*     (2006.01)

(52) U.S. Cl.
    CPC .......... *A61B 5/6823* (2013.01); *A61B 5/6898* (2013.01); *A61B 5/7282* (2013.01); *A61M 21/02* (2013.01); *G06F 19/3418* (2013.01); *G16H 10/20* (2018.01); *G16H 10/60* (2018.01); *G16H 15/00* (2018.01); *G16H 40/63* (2018.01); *G16H 40/67* (2018.01); *G16H 50/30* (2018.01); *A61B 5/01* (2013.01); *A61B 5/024* (2013.01); *A61B 5/0533* (2013.01); *A61B 5/087* (2013.01); *A61B 5/0816* (2013.01); *A61B 5/11* (2013.01); *A61B 5/1135* (2013.01); *A61B 5/14542* (2013.01); *A61B 5/486* (2013.01); *A61B 5/7203* (2013.01); *A61M 2021/0027* (2013.01)

(56) References Cited

U.S. PATENT DOCUMENTS

| | | | |
|---|---|---|---|
| 5,520,176 A | 5/1996 | Cohen | |
| 5,605,151 A | 2/1997 | Lynn | |
| 5,769,084 A | 6/1998 | Katz | |
| 5,891,023 A | 4/1999 | Lynn | |
| 5,958,902 A | 9/1999 | Meyer | |
| 6,062,216 A * | 5/2000 | Corn | A61B 5/113 128/204.23 |
| 6,223,064 B1 | 4/2001 | Lynn | |
| 6,329,352 B1 | 12/2001 | Meyer | |
| 6,342,039 B1 | 1/2002 | Lynn | |
| 6,529,752 B2 | 3/2003 | Krausman | |
| 6,811,538 B2 | 11/2004 | Westbrook | |
| 7,297,119 B2 | 11/2007 | Westbrook | |
| 7,324,845 B2 | 1/2008 | Mietus | |
| 7,486,979 B2 | 2/2009 | Matlock | |
| 7,654,948 B2 | 2/2010 | Kaplan | |
| 7,734,334 B2 | 6/2010 | Mietus | |
| 7,766,841 B2 | 8/2010 | Yamamoto | |
| 7,806,831 B2 | 10/2010 | Lavie | |
| 7,881,798 B2 | 2/2011 | Miesel | |
| 7,942,824 B1 * | 5/2011 | Kayyali | A61B 5/021 600/538 |
| 8,055,321 B2 | 11/2011 | Bernreuter | |
| 8,055,348 B2 | 11/2011 | Heruth | |
| 8,172,766 B1 | 5/2012 | Kayyali | |
| 8,308,661 B2 | 11/2012 | Miesel | |
| 8,332,038 B2 | 12/2012 | Heruth | |
| 8,333,696 B2 | 12/2012 | Levendowski | |
| 8,355,769 B2 | 1/2013 | Levendowski | |
| 8,401,626 B2 | 3/2013 | Mietus | |
| 8,403,848 B2 | 3/2013 | Mietus | |
| 8,417,305 B2 | 4/2013 | Dixon | |
| 8,478,412 B2 | 7/2013 | Ignagni | |
| 8,512,221 B2 | 8/2013 | Kaplan | |
| 8,545,416 B1 | 10/2013 | Kayyali | |
| 8,639,313 B2 | 1/2014 | Westbrook | |
| 2001/0018557 A1 | 8/2001 | Lynn | |
| 2002/0095076 A1 | 7/2002 | Krausman | |
| 2002/0099033 A1 | 7/2002 | Meyer | |
| 2002/0165462 A1 | 11/2002 | Westbrook | |
| 2002/0173707 A1 | 11/2002 | Lynn | |
| 2003/0004423 A1 | 1/2003 | Lavie | |
| 2004/0254493 A1 | 12/2004 | Chervin | |
| 2005/0027207 A1 | 2/2005 | Westbrook | |
| 2005/0085738 A1 * | 4/2005 | Stahmann | A61B 5/00 600/529 |
| 2005/0113646 A1 | 5/2005 | Solos | |
| 2005/0234518 A1 | 10/2005 | Heruth | |
| 2005/0256418 A1 | 11/2005 | Mietus | |
| 2007/0055115 A1 * | 3/2007 | Kwok | A61B 5/0031 600/300 |
| 2007/0142715 A1 | 6/2007 | Banet | |
| 2007/0276439 A1 | 11/2007 | Miesel | |
| 2008/0051669 A1 | 2/2008 | Meyer | |
| 2008/0071150 A1 | 3/2008 | Miesel | |
| 2008/0071326 A1 | 3/2008 | Heruth | |
| 2008/0119747 A1 | 5/2008 | Mietus | |
| 2008/0269583 A1 | 10/2008 | Reisfeld | |
| 2008/0269832 A1 | 10/2008 | Wong | |
| 2008/0319277 A1 | 12/2008 | Bradley | |
| 2009/0062628 A1 | 3/2009 | Yamamoto | |
| 2010/0016694 A1 | 1/2010 | Martin | |
| 2010/0031959 A1 | 2/2010 | Avidor | |
| 2010/0069762 A1 | 3/2010 | Mietus | |
| 2010/0094103 A1 * | 4/2010 | Kaplan | A61B 5/4809 600/301 |
| 2010/0191136 A1 | 7/2010 | Wolford | |
| 2010/0240982 A1 * | 9/2010 | Westbrook | A61B 5/087 600/391 |
| 2011/0092831 A1 | 4/2011 | Herscovici-Cohen | |
| 2011/0190599 A1 | 8/2011 | Wang | |
| 2011/0295083 A1 | 12/2011 | Doelling | |
| 2012/0022340 A1 | 1/2012 | Heruth | |
| 2012/0078069 A1 | 3/2012 | Melker | |
| 2012/0130201 A1 | 5/2012 | Jain | |
| 2012/0316411 A1 | 12/2012 | Benaron | |
| 2013/0131464 A1 | 5/2013 | Westbrook | |
| 2013/0144190 A1 | 6/2013 | Bruce | |
| 2013/0181832 A1 | 7/2013 | Landau | |
| 2015/0073289 A1 | 3/2015 | Lim | |

FOREIGN PATENT DOCUMENTS

| | | |
|---|---|---|
| WO | WO/1998/046245 A1 | 10/1998 |
| WO | WO/2001/064101 A1 | 9/2001 |
| WO | WO/2001/091631 A1 | 12/2001 |
| WO | WO/2002/043579 A2 | 6/2002 |
| WO | WO/2002/065901 A2 | 8/2002 |
| WO | WO/2004/112606 A1 | 12/2004 |
| WO | WO/2005/089647 A1 | 9/2005 |
| WO | WO/2006/037184 A1 | 4/2006 |
| WO | WO/2006/082589 A2 | 8/2006 |
| WO | WO/2006/082589 A3 | 8/2006 |
| WO | WO/2006/133548 A1 | 12/2006 |
| WO | WO/2007/008706 A2 | 1/2007 |
| WO | WO/2007/008706 A3 | 1/2007 |
| WO | WO/2008/107899 A1 | 9/2008 |
| WO | WO/2008/118951 A1 | 10/2008 |
| WO | WO/2008/132736 A2 | 11/2008 |
| WO | WO/2008/132736 A3 | 11/2008 |
| WO | WO/2009/144598 A1 | 12/2009 |
| WO | WO/2010/038119 A2 | 4/2010 |
| WO | WO/2010/107928 A2 | 9/2010 |

(56) References Cited

FOREIGN PATENT DOCUMENTS

| WO | WO/2011/082346 | A2 | 7/2011 |
| WO | WO/2011/097296 | A1 | 8/2011 |
| WO | WO/2011/150362 | A2 | 12/2011 |
| WO | WO/2012/156427 | A1 | 11/2012 |

OTHER PUBLICATIONS

Schreiner, Collin et al., Blood Oxygen Level Measurement with a chest-based Pulse Oximetry Prototype System NIBEC, University of Ulster, Newtownabbey, Co. Antrim, BT37 0QB, Northern Ireland, Computing in Cardiology 2010;37:537-540.
www.sleepio.com webpages, Sep. 6, 2013.
PCT International Search Report and Written Opinion, PCT/US2018/014033, dated Mar. 9, 2018.

* cited by examiner

| | |
|---|---|
| Gender | Female |
| Age | 50 years |
| DOB | 1962-09-12 |

Interview Questions

Medical Problems
- allergies

Medicines, especially meds taken before bedtime
- none

Bed partner?
- yes

*Figure 5*

Interview Questions

Biggest complaint about sleep?
- snoring

Is this your complaint or your bed partner's observation about you?
- bed partner How long has this been a problem?
- 5 years Typical bed time
10:30 PM Typical wake-up time
6:15 AM

*Figure 6*

Stop Bang

Do you Snore?
- ✓ yes
- ✗ no

Do you feel Tired or sleepy during the day?
- ✓ yes
- ✗ no

Has anyone Observed you stop breathing?
- ✓ yes
- ✗ no

Do you have high blood Pressure?
- ✓ yes
- ✗ no

Is your Body mass index over 35?
- ✓ yes
- ✗ no
- BMI

Is your Age over 50?
- ✓ yes
- ✗ no

*Figure 7*

Verizon 3G 10:37 AM

[Back] Epworth Sleepiness Scale

1 = slight chance of dozing
2 = moderate chance of dozing
3 = high chance of dozing
It is important that you answer each question as best you can Situation Chance of Dozing (0-3):

○ Sitting and reading

| 0 | 1 | 2 | 3 |

○ Watching TV

| 0 | 1 | 2 | 3 |

○ Sitting, inactive in a public place (e.g. a theater or a meeting)

| 0 | 1 | 2 | 3 |

○ As a passenger in a car for an hour without a break

*Figure 8*

| | |
|---|---|
| ..ıl_Verizon 3G | 10:41 AM |

‹ Reports   Sleep Log Report

| | |
|---|---|
| Oct 2012<br><br>28 | Sleep Time: 02:00 AM<br>Wake-up Time: 06:30 AM<br>Total no. of awakenings: 3<br>Sleeping Time: 3:30 hrs<br>Sleep efficiency: 42% |
| Oct 2012<br><br>29 | Sleep Time: 12:00 AM<br>Wake-up Time: 04:30 AM<br>Total no. of awakenings: 1<br>Sleeping Time: 4:15 hrs<br>Sleep efficiency: 56% |
| Oct 2012<br><br>30 | Sleep Time: 11:00 PM<br>Wake-up Time: 06:00 AM<br>Total no. of awakenings: 2<br>Sleeping Time: 6:00 hrs<br>Sleep efficiency: 80% |
| Nov 2012 | Sleep Time: 12:00 AM<br>Wake-up Time: 07:30 AM |

*Figure 22*

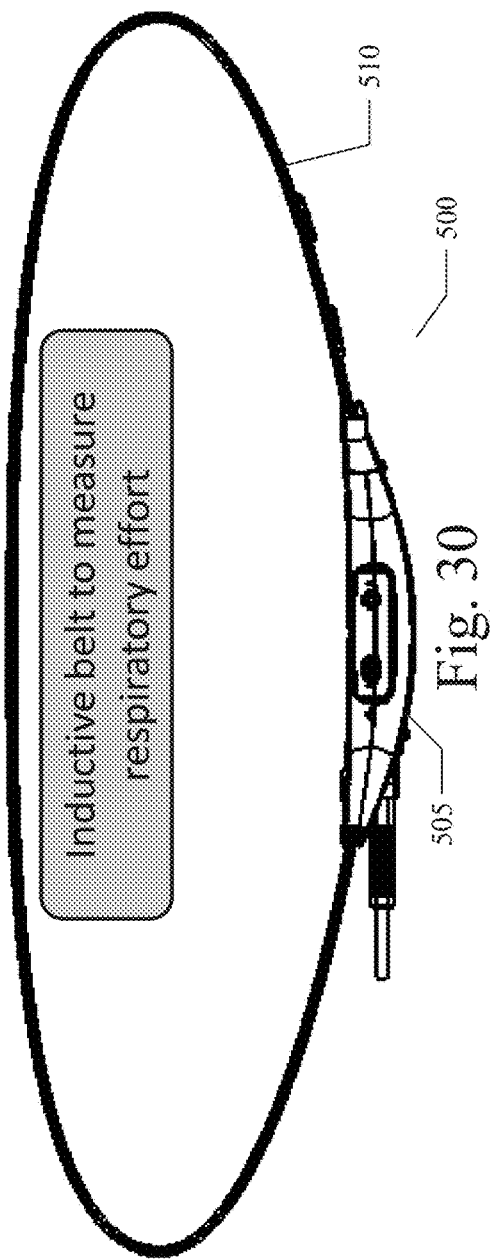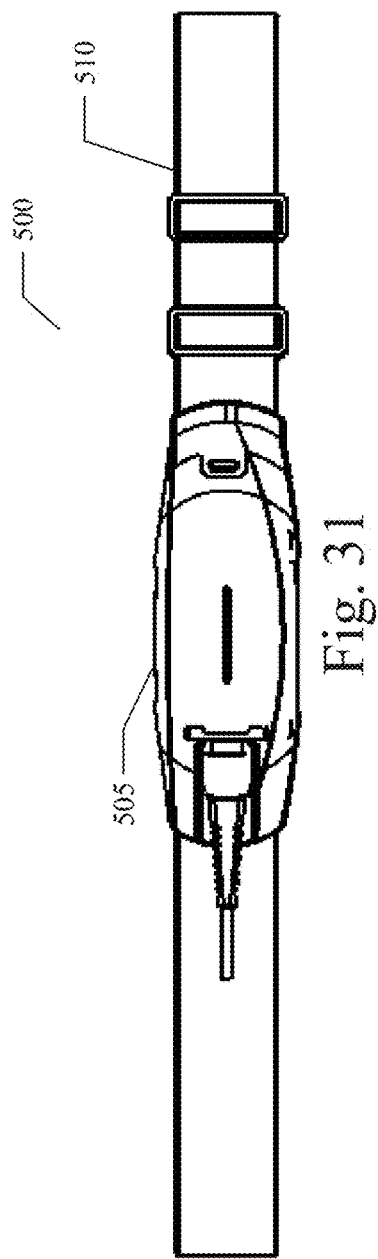

SYSTEM AND METHOD FOR SLEEP DISORDER DIAGNOSIS AND TREATMENT

PRIORITY PATENT APPLICATION

This is a continuation-in-part patent application drawing priority from U.S. patent application Ser. No. 14/020,741; filed Sep. 6, 2013. This present patent application draws priority from the referenced patent application. The entire disclosure of the referenced patent application is considered part of the disclosure of the present application and is hereby incorporated by reference herein in its entirety.

TECHNICAL FIELD

This patent application relates to computer-implemented software and networked systems, according to one embodiment, and more specifically to a system and method for sleep disorder diagnosis and treatment.

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2012-2016 Somnology, Inc., All Rights Reserved.

BACKGROUND

Sleep disorders are extremely common in the general population, with estimates of 15 million adults in the U.S. with persistent insomnia, and another 24 million adults and children suffering from obstructive sleep apnea. The current model of care is for people to seek consultation with their primary care doctor first about their sleep issues. From there, people are referred for sleep studies, sleep specialists, or given medications. Treatment is often delayed, involves potentially habit-forming if medications, or is too expensive to pursue.

Smartphones are becoming the predominant link between data and people. Most current smartphones provide a capability to use mobile software applications (apps). A mobile software application (app) can embody a defined set of functionality and can be installed and executed on a mobile device, such as a smartphone, a tablet device, laptop computer, or other form of mobile computing or communications device. Conventional mobile apps are available that focus on one narrow aspect or another of different sleep problems. However, these conventional mobile apps do not integrate a set of diagnostic and therapeutic tools to fully assess and treat a user's sleep disorder. For example, current systems do not integrate a user's sleep history in a diagnostic and treatment system. Additionally, one may find a mobile app that plays soothing music, or another that wakes the user up at a particular time, or another that records snoring. However, these systems cannot combine data obtained in a diagnostic phase for use in a sleep disorder treatment phase.

SUMMARY

The various embodiments described herein offer a solution to the problems identified above by providing an interactive interview with the user, then guiding users to possible sleep disorder diagnoses and treatments. If the user shows signs of insomnia, the app instructs the user in behavioral therapy, provides a sleep log tool to monitor progress, and gives feedback to the user about their progress, following established clinical guidelines for treatment. If the user shows signs of obstructive sleep apnea, the user may employ the breathing disturbance monitoring device described herein to measure respiratory patterns at night. Screening studies for sleep apnea are integrated within the app itself. All the tools contained in the various embodiments described herein educate the user about their sleep problem and provide immediate assistance—with ease of use and for a low cost.

The various embodiments described herein provide a software application that includes among the following features:

a. An automated and prompted sleep interview similar to an interview a patient might receive in a doctor's office.
b. Feedback to the user based on the user's answers in the prompted sleep interview.
c. Guidance through behavioral treatment programs, including Stimulus Control Therapy and Sleep Restriction Therapy. The treatment programs for a particular user are customized and based on information gathered from the user and diagnoses automatically determined from the prompted sleep interview.
d. A sleep log meter so the user can keep track of sleep patterns in quantitative way.
e. Soundscapes to assist the user to achieve a relaxed state before bed and whenever the user cannot fall asleep.
f. Automated information presentations that describe possible sleep diagnoses in more detail, typical diagnostic tests, various treatment options, and the five closest sleep centers to the user's location.
g. Rewards Center where the user can redeem points collected for keeping sleep logs or for completing other actions to which incentives are tied. The user can redeem points for prizes, such as animal dream totems, exclusive musical recordings, additional soundscapes, and the like.
h. Breathing Disturbance Meter integration, which measures respiratory breathing patterns at night to screen for possible obstructive sleep apnea.
i. All graphs and questionnaires may be exported as PDF files and emailed to the user and/or a doctor.
j. The diagnostic and treatment features of the various embodiments were designed by a board certified sleep specialist.

The combinations of features described and claimed herein do not exist in an integrated and coordinated manner in any other app or software product with a single focus—to help more people at the lowest cost possible to sleep better and therefore perform better.

BRIEF DESCRIPTION OF THE DRAWINGS

The various embodiments are illustrated by way of example, and not by way of limitation, in the figures of the accompanying drawings in which:

FIGS. 5 through 8 illustrate an example embodiment, implemented as a mobile app, which shows various questionnaire display screens of the user interface of the example embodiment;

FIGS. 21 through 25 illustrate an example embodiment, implemented as a mobile app, which shows various report display screens of the user interface of the example embodiment;

FIGS. 30 and 31 illustrate an example embodiment of the inductive belt component of the sleep metering system of an example embodiment;

DETAILED DESCRIPTION

Figure 1:
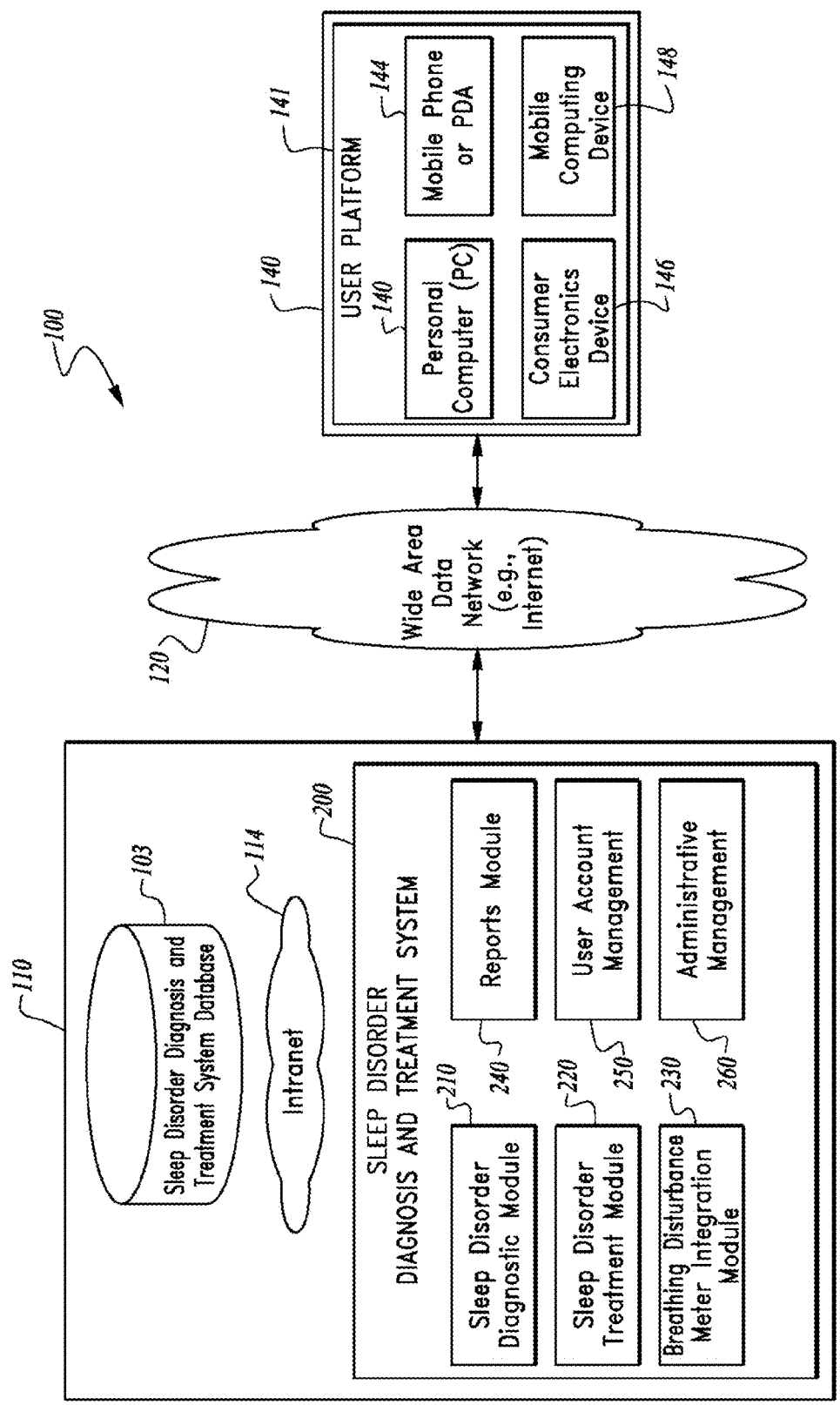
FIG. 1 illustrates an example embodiment of a sleep disorder diagnosis and treatment system as a hosted application.

In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, a system and method for sleep disorder diagnosis and treatment are disclosed. The various embodiments provide the ability to integrate a set of diagnostic and therapeutic tools to fully assess and treat a user's sleep disorder in a convenient and low cost mobile platform. In various embodiments described in detail below, a software application program is used to generate and enable the sleep disorder diagnosis and treatment system interface using a computer system, a web appliance, and/or a mobile device. As described in more detail below, the computer or computing system on which the described embodiments can be implemented can include personal computers (PCs), portable computing devices, laptops, tablet computers, personal digital assistants (PDAs), personal communication devices (e.g., cellular telephones, smartphones, or other wireless devices), network computers, set-top boxes, consumer electronic devices, or any other type of computing, data processing, communication, networking, or electronic system.

A mobile version of an example embodiment provides a user-friendly interface from which the user can easily view and interact with the various information presentations and prompts from a mobile device. As described in more detail below, a mobile software application (app) embodying a mobile version of an example embodiment as described herein can be installed and executed on a mobile device, such as a smartphone, a tablet device, laptop computer, or other form of mobile computing or communications device. In another embodiment, a website can be used as a hosted service provider without installing any software on the mobile device. In this embodiment, a user can use the features described herein just by directing a browser to the website host through the use of the preinstalled or installed browser. These embodiments are described in more detail below. In an example embodiment, a splash screen appears whenever the user opens or launches the mobile application on the mobile device. This splash screen displays a host logo while opening the login screen or the live feed.

User log-in functionality in the mobile app provides a user-friendly user interface in which the user provides the email address and password associated with the user account. If the user does not have an account, the user can create an account from this user interface. The process of creating a user account is simple and only requires the user to provide the following information: name, surname, e-mail address, and password. By completing this information, the user can create an account and get access to customized sleep disorder diagnosis and treatment information.

Referring now to FIG. 1, in an example embodiment 100, a system and method for sleep disorder diagnosis and treatment are disclosed. In one example embodiment, an application or service, typically provided by or operating on a host site (e.g., a website) 110, is provided to simplify and facilitate the downloading or hosted use of the sleep disorder diagnosis and treatment system 200 of an example embodiment. In a particular embodiment, the sleep disorder diagnosis and treatment system 200 can be downloaded from the host site 110 by a user at a user platform 140. Alternatively, the sleep disorder diagnosis and treatment system 200 can be hosted by the host site 110 for a networked user at a user platform 140. The details of the sleep disorder diagnosis and treatment system 200 of an example embodiment are provided below.

Referring again to FIG. 1, the sleep disorder diagnosis and treatment system 200 can be hosted by host site 110 and be in network communication with a plurality of user platforms 140. The host site 110 and user platforms 140 may communicate and transfer data and information in the data network ecosystem 100 shown in FIG. 1 via a wide area data network (e.g., the Internet) 120. Various components of the host site 110 can also communicate internally via a conventional intranet or local area network (LAN) 114.

Networks 120 and 114 are configured to couple one computing device with another computing device. Networks 120 and 114 may be enabled to employ any form of computer readable media for communicating information from one electronic device to another. Network 120 can include the Internet in addition to LAN 114, wide area networks (WANs), direct connections, such as through an Ethernet port or a universal serial bus (USB) port, other forms of computer-readable media, or any combination thereof. On an interconnected set of LANs, including those based on differing architectures and protocols, a router and/or gateway device acts as a link between LANs, enabling messages to be sent between computing devices. Also, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communication links known to those of ordinary skill in the art. Furthermore, remote computers and other related electronic devices can be remotely connected to either LANs or WANs via a wireless link, WiFi, Bluetooth, satellite, or modem and temporary telephone link.

Networks 120 and 114 may further include any of a variety of wireless sub-networks that may further overlay stand-alone ad-hoc networks, and the like, to provide an infrastructure-oriented connection. Such sub-networks may include mesh networks, Wireless LAN (WLAN) networks, cellular networks, and the like. Networks 120 and 114 may also include an autonomous system of terminals, gateways, routers, and the like connected by wireless radio links or wireless transceivers. These connectors may be configured to move freely and randomly and organize themselves arbitrarily, such that the topology of networks 120 and 114 may change rapidly and arbitrarily.

Networks 120 and 114 may further employ a plurality of access technologies including 2nd (2G), 2.5, 3rd (3G), 4th (4G) generation radio access for cellular systems, WLAN, Wireless Router (WR) mesh, and the like. Access technologies such as 2G, 3G, 4G, and future access networks may enable wide area coverage for mobile devices, such as one or more of client devices 141, with various degrees of mobility. For example, networks 120 and 114 may enable a radio connection through a radio network access such as Global System for Mobile communication (GSM), General Packet Radio Services (GPRS), Enhanced Data GSM Environment (EDGE), Wideband Code Division Multiple Access (WCDMA), CDMA2000, and the like. Networks 120 and 114 may also be constructed for use with various other wired and wireless communication protocols, including TCP/IP, UDP, SIP, SMS, RTP, WAP, CDMA, TDMA, EDGE, UMTS, GPRS, GSM, UWB, WiFi, WiMax, IEEE 802.11x, and the like. In essence, networks 120 and 114 may include virtually any wired and/or wireless communication mechanisms by which information may travel between one computing device and another computing device, network, and the like. In one embodiment, network 114 may represent a LAN that is configured behind a firewall (not shown), within a business data center, for example.

The sleep disorder diagnosis and treatment system can be implemented using any form of network transportable digital data. The network transportable digital data can be transported in any of a group of file formats, protocols, and associated mechanisms usable to enable a host site 110 and a user platform 140 to transfer data over a network 120. In one embodiment, the data format for the user interface can be HyperText Markup Language (HTML). HTML is a common markup language for creating web pages and other information that can be displayed in a web browser. In another embodiment, the data format for the user interface can be Extensible Markup Language (XML). XML is a markup language that defines a set of rules for encoding interfaces or documents in a format that is both human-readable and machine-readable. In another embodiment, a JSON (JavaScript Object Notation) format can be used to stream the interface content to the various user platform 140 devices. JSON is a text-based open standard designed for human-readable data interchange. The JSON format is often used for serializing and transmitting structured data over a network connection. JSON can be used in an embodiment to transmit data between a server, device, or application, wherein JSON serves as an alternative to XML.

In a particular embodiment, a user platform 140 with one or more client devices 141 enables a user to access data and provide data for the sleep disorder diagnosis and treatment system 200 via the host 110 and network 120. Client devices 141 may include virtually any computing device that is configured to send and receive information over a network, such as network 120. Such client devices 141 may include portable devices 144, such as, cellular telephones, smartphones, display pagers, radio frequency (RF) devices, infrared (IR) devices, global positioning devices (GPS), Personal Digital Assistants (PDAs), handheld computers, wearable computers, tablet computers, integrated devices combining one or more of the preceding devices, and the like. Client devices 141 may also include other computing devices, such as personal computers 142, multiprocessor systems, microprocessor-based or programmable consumer electronics, network PC's, and the like. Client devices 141 may also include other processing devices, such as consumer electronic (CE) devices 146 and/or mobile computing devices 148, which are known to those of ordinary skill in the art. As such, client devices 141 may range widely in terms of capabilities and features. For example, a client device configured as a cell phone may have a numeric keypad and a few lines of monochrome LCD display on which only text may be displayed. In another example, a web-enabled client device may have a touch sensitive screen, a stylus, and many lines of color LCD display in which both text and graphics may be displayed. Moreover, the web-enabled client device may include a browser application enabled to receive and to send wireless application protocol messages (WAP), and/or wired application messages, and the like. In one embodiment, the browser application is enabled to employ HyperText Markup Language (HTML), Dynamic HTML, Handheld Device Markup Language (HDML), Wireless Markup Language (WML), WMLScript, JavaScript™, EXtensible HTML (xHTML), Compact HTML (CHTML), and the like, to display and/or send digital information. In other embodiments, mobile devices can be configured with applications (apps) with which the functionality described herein can be implemented.

Client devices 141 may also include at least one client application that is configured to send and receive content data or/and control data from another computing device via a wired or wireless network transmission. The client application may include a capability to provide and receive textual data, graphical data, video data, audio data, and the like. Moreover, client devices 141 may be further configured to communicate and/or receive a message, such as through an email application, a Short Message Service (SMS), direct messaging (e.g., Twitter™), Multimedia Message Service (MMS), instant messaging (IM), internet relay chat (IRC), mIRC, Jabber, Enhanced Messaging Service (EMS), text messaging, Smart Messaging, Over the Air (OTA) messaging, or the like, between another computing device, and the like.

As one option, the sleep disorder diagnosis and treatment system 200, or a portion thereof, can be downloaded to a user device 141 of user platform 140 and executed locally on a user device 141 (e.g., see FIG. 2 described below). The downloading of the sleep disorder diagnosis and treatment system 200 application (or a portion thereof) can be accomplished using conventional software downloading functionality. As a second option, the sleep disorder diagnosis and treatment system 200 can be hosted by the host site 110 and executed remotely, from the user's perspective, on host system 110. In one embodiment, the sleep disorder diagnosis and treatment system 200 can be implemented as a service in a service-oriented architecture (SOA) or in a Software-as-a-Service (SAAS) architecture. In any case, the functionality performed by the sleep disorder diagnosis and treatment system 200 is as described herein, whether the application is executed locally or remotely, relative to the user.

Referring again to FIG. 1, the sleep disorder diagnosis and treatment system 200 of an example embodiment is shown to include a sleep disorder diagnosis and treatment system database 103. The database 103 is used in an example embodiment for data storage of information related to the sleep disorder diagnosis and treatment of users, the sleep logs of users, communications between users and host representatives, shared documents, images, soundscapes, metadata, and the control data for managing the user interactions and the associated user interfaces. It will be apparent to those of ordinary skill in the art that the database 103 can be used for the storage of a variety of data in support of the sleep disorder diagnosis and treatment system 200 of an example embodiment.

Figure 2:
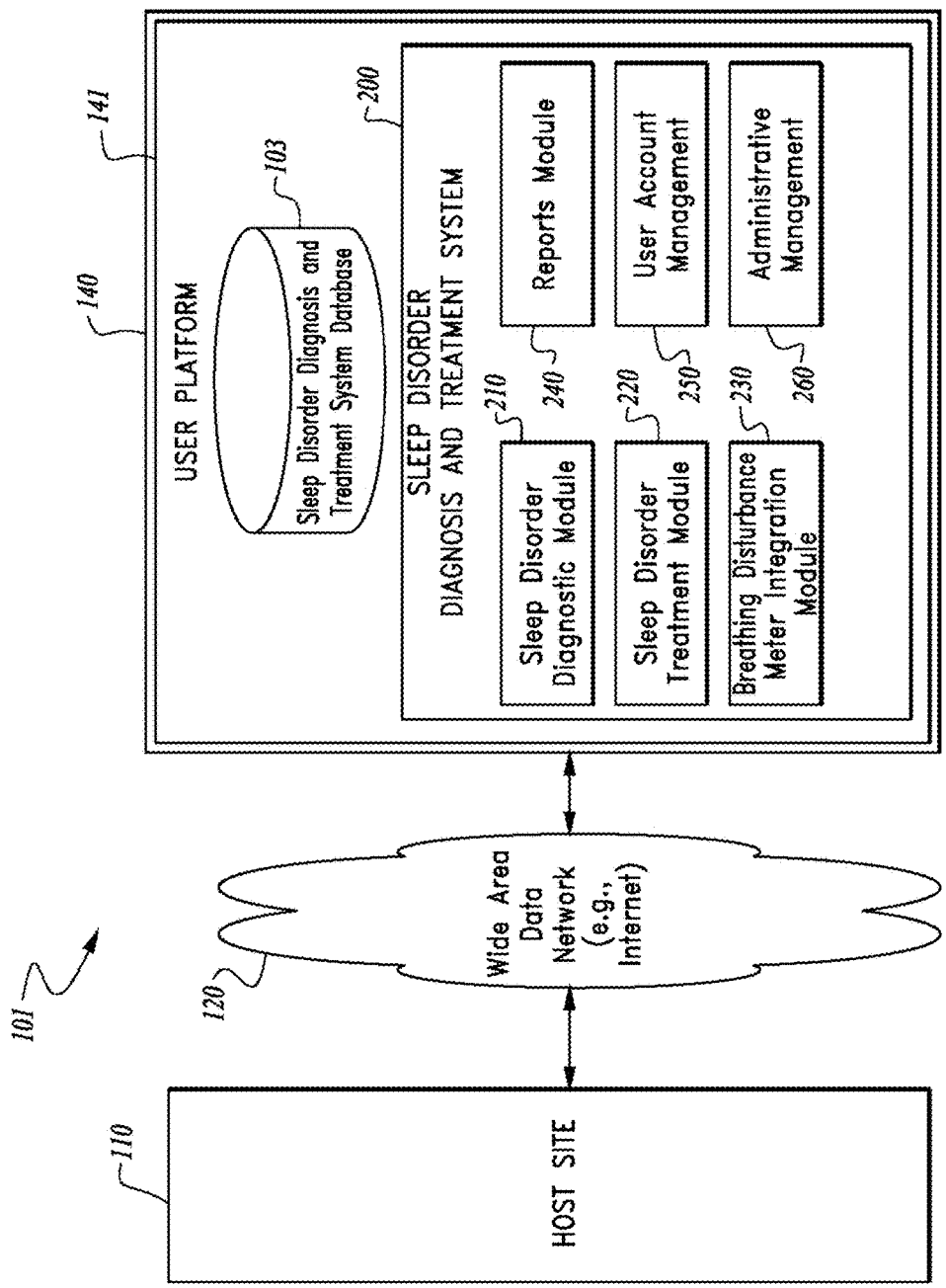
FIG. 2 illustrates an alternative example embodiment of a sleep disorder diagnosis and treatment system as a downloaded application.

Referring to FIG. 2, an alternative embodiment 101 is shown in which the sleep disorder diagnosis and treatment system 200 and associated database 103 can be downloaded and executed locally at a user device 141 of user platform 140. In other embodiments, portions of system 200 and/or database 103 can be executed locally at a user device 141 of user platform 140 or executed remotely at the host site 110. In each of these implementations, the functionality and structure of the sleep disorder diagnosis and treatment system 200 of an example embodiment is similar to the example embodiments described herein.

Referring again to FIGS. 1 and 2, an example embodiment is shown to include a sleep disorder diagnosis and treatment system 200. Sleep disorder diagnosis and treatment system 200 can include a sleep disorder diagnostic module 210, a sleep disorder treatment module 220, a Breathing Disturbance Meter integration module 230, a reports module 240, a user account management module 250, and an administrative management module 260. Each of these modules can be implemented as software components executing within an executable environment of sleep disorder diagnosis and treatment system 200 operating on host site 110 or user platform 140. Each of these modules of an example embodiment is described in more detail below in connection with the figures provided herein.

Referring again to FIGS. 1 and 2, the sleep disorder diagnosis and treatment system 200 of an example embodiment is shown to include a sleep disorder diagnostic module 210. The sleep disorder diagnostic module 210 can be used to query information from a user and to use the information to make a sleep disorder diagnosis. In particular, the sleep disorder diagnostic module 210 can be used to present, prompt, and process user input on various user questionnaires. The user questionnaires include sleep-related interview questions and a STOPBANG questionnaire. The STOPBANG questionnaire screens for signs of Obstructive Sleep Apnea (OSA). STOPBANG is an acronym representing the symptoms that can be indicative of OSA: Snoring, Feeling Tired, Observed pauses in breathing, High blood Pressure, Body mass index greater than 35, Age greater than 50, Neck circumference greater than 40 cm (16 in), Male Gender, or post-menopausal female. Three or more positive answers from the user on the STOPBANG questionnaire are considered potentially indicative of OSA.

The sleep disorder diagnostic module 210 can be configured to generate a user interface to prompt a user for input on various questionnaires related to the user's sleep patterns.

Based on the user's input, the sleep disorder diagnostic module 210 can determine whether or not the user is showing signs or symptoms of common sleep disorders. These questionnaires are not designed to provide a certain diagnosis. Rather, the sleep disorder diagnostic module 210 can process the user responses and automatically determine if the user is showing signs that suggest a possible sleep disorder or a possible sleep-related breathing problem. In this case, the sleep disorder diagnostic module 210 can signal the sleep disorder treatment module 220 to suggest particular sleep disorder treatments or OSA-related treatments. The sleep disorder diagnostic module 210 can be configured to store the user's responses to enable the user to share the responses later with a health care provider. The sleep disorder diagnostic module 210 can also be configured to use these questionnaires and related responses to start a discussion with the user's health care provider on associated sleep issues to determine whether a particular treatment is needed. If treatment is indicated, the sleep disorder treatment module 220 can be configured to recommend a type of treatment.

Figure 3:
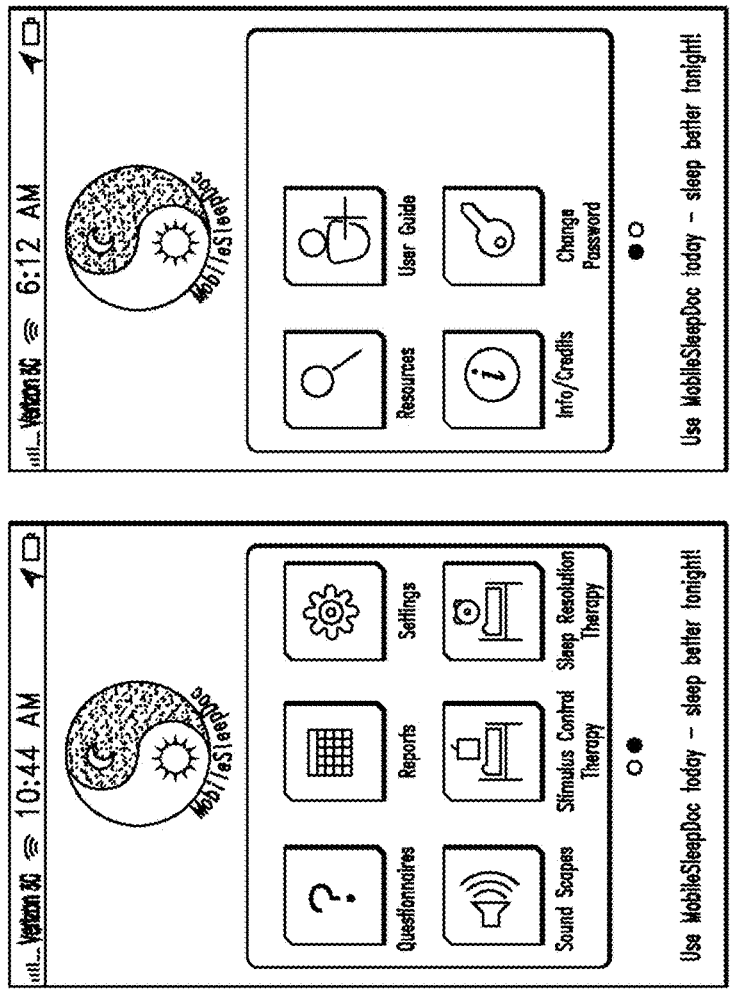
FIG. 3 illustrates an example embodiment, implemented as a mobile device application (mobile app), that shows a home display screen of the user interface of the example embodiment.
Figure 4:
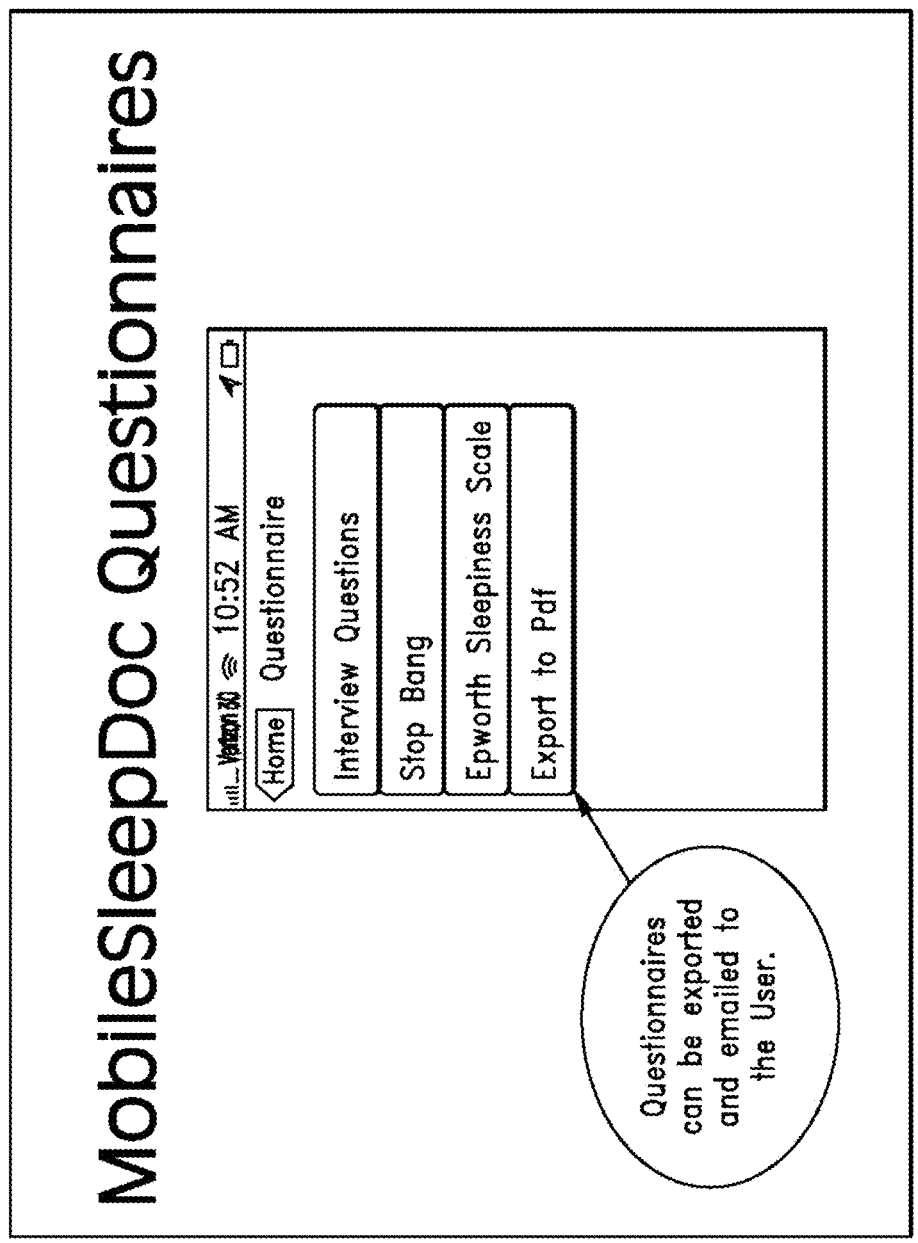
FIG. 4 illustrates an example embodiment, implemented as a mobile app, which shows an initial questionnaire display screen of the user interface of the example embodiment.

Referring now to FIG. 3, an example embodiment, implemented as a mobile device application (mobile app), shows a splash screen or home display screen of the user interface of the example embodiment. The home display screen is displayed on a user's mobile device when the mobile app is launched. FIG. 4 illustrates an example embodiment, implemented as a mobile app, which shows an initial questionnaire display screen of the user interface of the example embodiment. The initial questionnaire display screen can be presented when the user activates a particular icon presented in the home display screen.

FIGS. 5 through 8 illustrate an example embodiment, implemented as a mobile app, which shows various questionnaire display screens of the user interface of the example embodiment. The series of questionnaires presented by the sleep disorder diagnostic module 210 prompt the app user for basic demographic information, such as age and date of birth. The various questionnaires also contain questions related to the user's sleep habits, such as the user's typical bedtime and whether the user takes any medications before bed. These are important questions that can affect the quality of sleep. The sleep interview presented and managed by the sleep disorder diagnostic module 210 serves as a starting point for a discussion and potential diagnosis of the user's sleep patterns. Based on the user's input, the sleep disorder diagnostic module 210 can determine whether or not the user is showing signs or symptoms of common sleep disorders. The sleep disorder diagnostic module 210 can signal the sleep disorder treatment module 220 to suggest to the user and/or select for the user particular sleep disorder treatments or OSA-related treatments.

Referring to FIG. 8, the sleep disorder diagnostic module 210 can also be used to present, prompt, and process user input on an Epworth Sleepiness Scale. The Epworth Sleepiness Scale (ESS) is a scale intended to assess daytime sleepiness that is measured by use of a very short questionnaire. The ESS measures how likely the user is to fall asleep as rated on a scale from 0 to 3, with 0 being not at all likely and 3 being very likely. A cumulative score of ten or higher on this scale suggests that the user is abnormally sleepy, and may point to an underlying sleep disorder. This can be helpful in diagnosing sleep disorders. The ESS was introduced in 1991 by Dr. Murray Johns of Epworth Hospital in Melbourne, Australia.

Referring again to FIGS. 1 and 2, the sleep disorder diagnosis and treatment system 200 of an example embodiment is shown to include a sleep disorder treatment module 220. The sleep disorder treatment module 220 can be used to suggest to the user and/or select for the user particular sleep disorder treatments or OSA-related treatments based on the user responses captured and processed by the sleep disorder diagnostic module 210. In an example embodiment, these sleep disorder therapies or treatments can include: 1) behavioral therapies, 2) stimulus control therapy (SCT), 3) sleep restriction therapy (SRT), sleep logs, and sleep efficiency assessments, and 4) soundscapes. These various therapies as implemented by the sleep disorder treatment module 220 of an example embodiment are described in more detail below.

Behavioral therapies are treatments that focus on changing a person's behavior in order to treat a condition. The goal of behavioral therapy is to reinforce beneficial behaviors and discourage behaviors that are harmful or unhelpful. Behavioral therapies encourage the user to create healthy habits and to break unhealthy ones.

Behavioral therapy for insomnia may include a cognitive component, and thus is termed Cognitive Behavioral Therapy, or CBT. CBT is designed to change behaviors by focusing on how people think and feel about their behaviors and their disorder. CBT is meant to address negative emotions, such as anxiety or depression that may be associated with having a disorder. CBT also explores the thought processes that people go through while engaging in unhealthy behaviors and habits, which may indicate why they engage in those behaviors. The goal of CBT is to address the root causes of unhealthy behaviors and habits (i.e., negative emotions and thought processes), so that these behaviors can be replaced by healthier, more positive ones. The sleep disorder treatment module 220 can be used to guide the user through various CBT treatments based on the assessment of their condition as determined by the sleep disorder diagnostic module 210. The example embodiment focuses on behavioral therapies because these therapies are safer and longer-lasting than sleep medications, and may be started or re-started at any time. In contrast to some types of sleeping pills or other medications, behavioral therapy does not result in a "tolerance" that limits continued benefit. The sleep disorder treatment module 220 recognizes that changing established behaviors is very difficult. That's why the app provides positive feedback to encourage users to keep trying. The sleep disorder treatment module 220 includes several therapies that teach users to help themselves sleep better. The sleep disorder treatment module 220 also presents, prompts, and retains sleep logs so users can keep track of their sleep disorder treatment progress. The sleep logs and the related reports are generated by the sleep disorder treatment module 220 and the reports module 240. The goal of the various embodiments and treatment strategies is to help increase the quality of sleep in meaningful and lasting ways.

Figure 9:
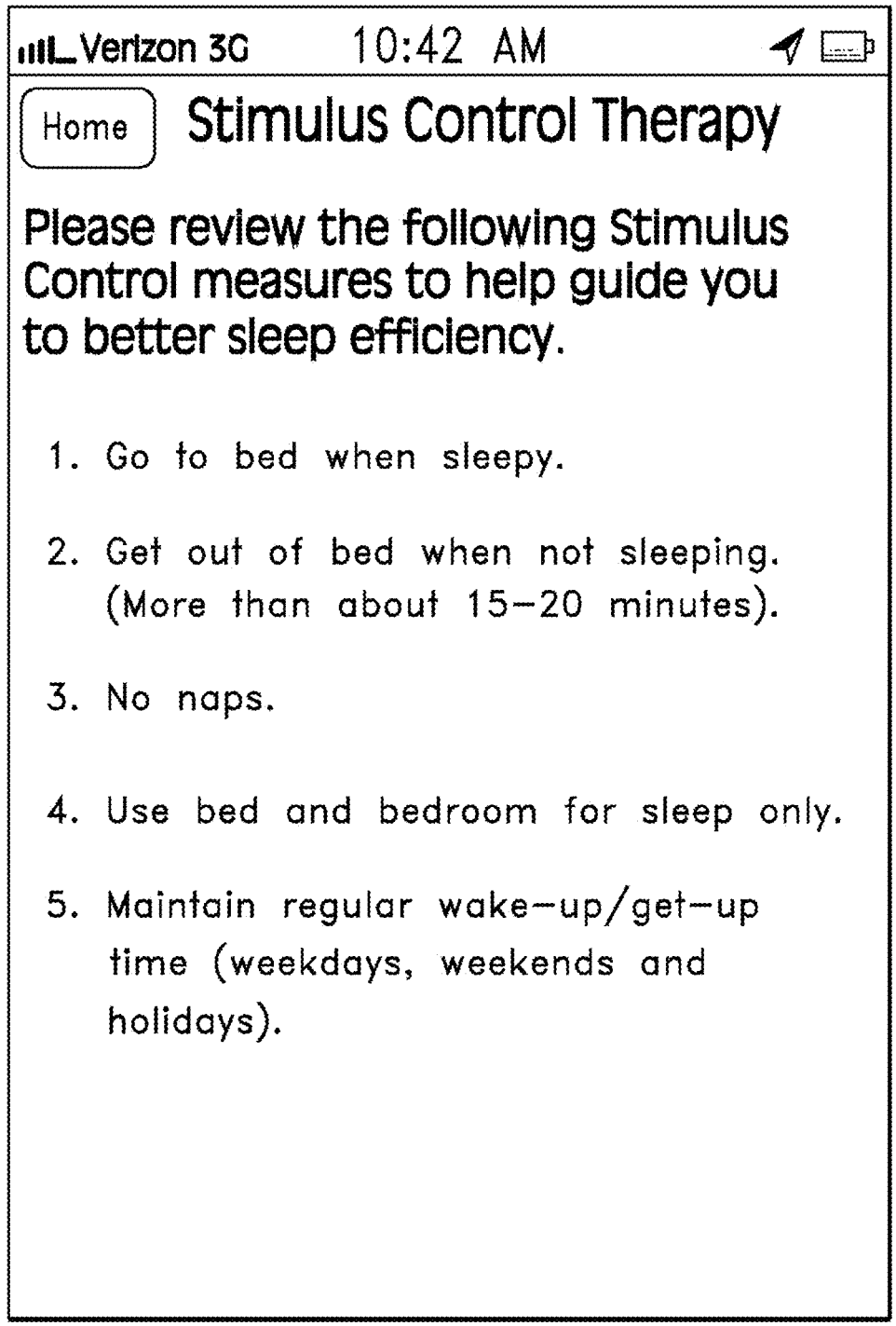
FIG. 9 illustrates an example embodiment, implemented as a mobile app, which shows a stimulus control therapy display screen of the user interface of the example embodiment.

FIG. 9 illustrates an example embodiment, implemented as a mobile app, which shows a stimulus control therapy display screen of the user interface of the example embodiment. As part of the treatment or therapy options provided by the sleep disorder treatment module 220, a Stimulus Control Therapy, or SCT, is used to treat insomnia. In the example embodiment, there are five main principles of SCT:
  a. Go to bed when sleepy, not when you think you should go to bed.
  b. Get out of bed when not sleeping. Do not stay in bed for more than 15-20 minutes, even if you are actively trying to sleep.
  c. No naps.

d. Use bed and bedroom for sleep (or sexual intimacy) only.
e. Maintain a regular wake-up/get-up time (on weekdays, weekends, and holidays).

One of the goals of SCT is to help the user associate the bed and bedroom with sleep rather than the inability to sleep. Another goal is to help the user break habits that keep the vicious cycle of insomnia going, such as staying in bed half of the day to try to "catch up" on lost sleep. SCT helps the user to create new, healthy habits, and encourages the user to maintain a regular sleep/wake cycle. As part of this encouragement, the sleep disorder treatment module 220 guides the user through a set of display screens, information presentations, and prompts. For example, FIG. 9 illustrates how the user can transition from the home display screen to a set of SCT display screens. The SCT display screen section allows the user to review the SCT guidelines and reminds the user of the guidelines before bedtime. The user is prompted to create, follow, and assess their sleep logs using SCT to determine if their sleep problems can be resolved with this treatment intervention. In a particular embodiment, the sleep logs can be accessed through the reports page.

Figure 10:
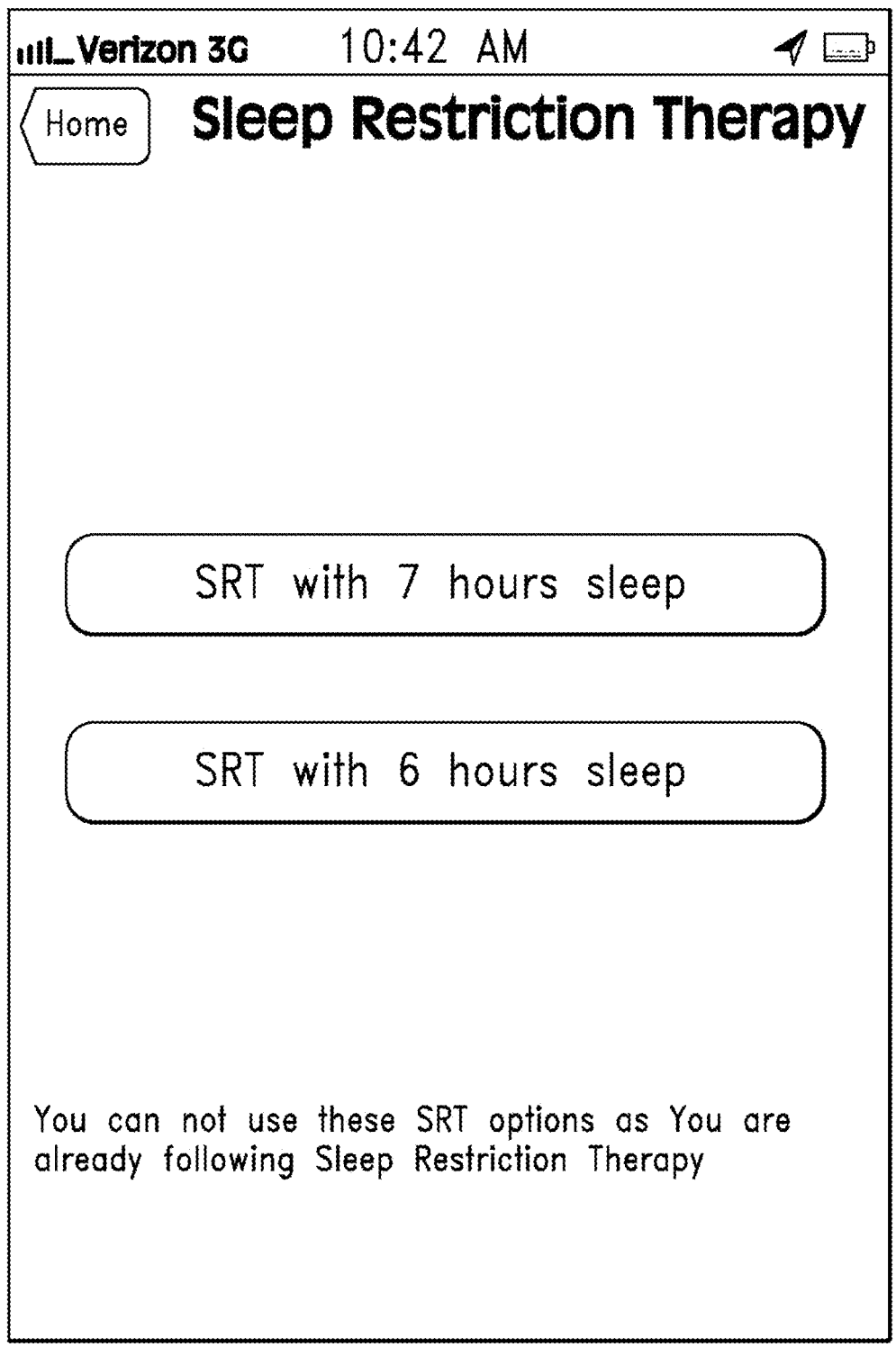
FIG. 10 illustrates an example embodiment, implemented as a mobile app, which shows a sleep restriction therapy display screen of the user interface of the example embodiment.

FIG. 10 illustrates an example embodiment, implemented as a mobile app, which shows a sleep restriction therapy display screen of the user interface of the example embodiment. As part of the treatment or therapy options provided by the sleep disorder treatment module 220, a next level of behavioral therapy for insomnia is Sleep Restriction Therapy (SRT). SRT is a treatment program that uses controlled sleep deprivation as a therapy. Sleep deprivation is used as a tool to help the user fall asleep and stay asleep. In a typical treatment scenario as guided by the sleep disorder treatment module 220, the user can begin by choosing an SRT program with seven hours of sleep a night or an SRT program with six hours of sleep a night. If the user has already started SRT and is in the middle of an SRT monitoring period, the user cannot start a new program. It will be apparent to those of ordinary skill in the art that SRT programs with other sleep time periods (e.g., other than six or seven hours of sleep a night) can also be implemented. As part of the SRT program, the user is prompted to set their desired wake-up time as guided by the sleep disorder treatment module 220. Then, the sleep disorder treatment module 220 can assign a bedtime for the user that is six or seven hours prior to the desired wake-up time (depending on the SRT program time period selected by the user). The sleep disorder treatment module 220 can remind the user to wind down an hour before assigned bedtime, so that the user will be calm and not over-stimulated when they try to go to sleep.

Figure 11:
FIGS. 11 and 12 illustrate an example embodiment, implemented as a mobile app, which shows sleep log display screens of the user interface of the example embodiment.
Figure 12:
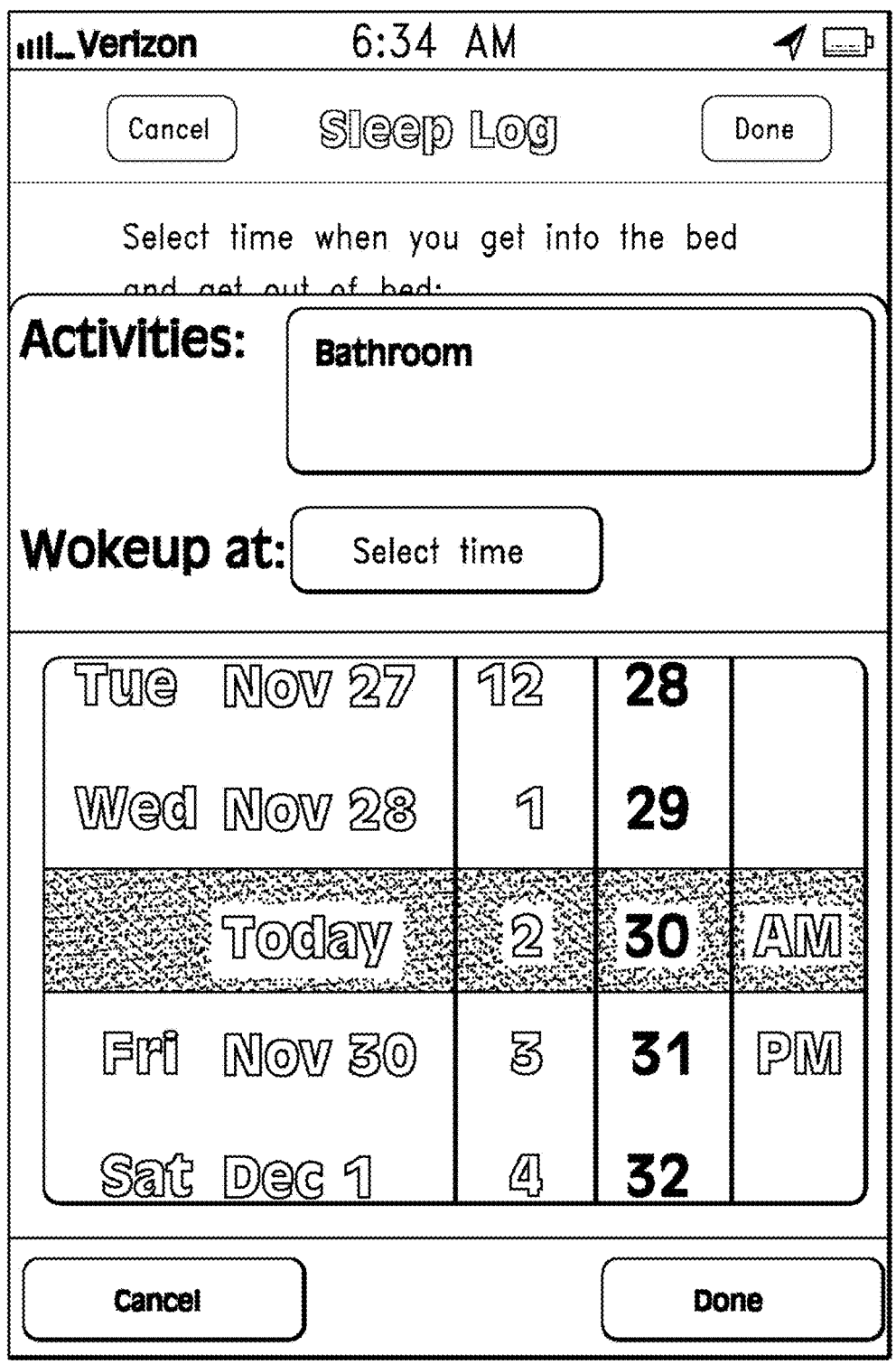

FIGS. 11 and 12 illustrate an example embodiment, implemented as a mobile app, which shows sleep log display screens of the user interface of the example embodiment. As guided by the sleep disorder treatment module 220, the user can enter their sleep log information by clicking on the right upper corner of a reports page screen presented by the reports module 240. Each morning, the user can use the sleep log to indicate when they got into bed and when they got out of bed, and when they actually fell asleep and when they woke up. As shown in FIG. 11, the user can make these entries in the sleep log by sliding the icons along the bars as shown. Once the user enters this information, the sleep disorder treatment module 220 can highlight in dark blue the hours the user was in the bed as shown in FIG. 11. If the user experienced awakenings in the middle of the night, the user may tap on each of the highlighted hour-long units individually to add details, such as the exact time the user woke up, how long the user was awake, and what occurred during each awakening as shown in FIG. 12. Using all the information entered into the sleep log by the user, the sleep disorder treatment module 220 can calculate the user's sleep efficiency. In an example embodiment, the sleep efficiency can be calculated as the percentage of time the user was in bed relative to the time spent by the user actually sleeping. The goal for nominal sleep efficiency is a percentage equal to or greater than 85%.

Although improvement in sleep quality is the ultimate goal for most people, improvement in sleep efficiency is a primary goal. Sleep efficiency is the sleep feature directly changeable by changing a person's behavior. It turns out that for most people, improvement in sleep quality follows improvement in sleep efficiency. If this is not the case, then another sleep problem may be present, like OSA or another diagnosis.

Once the user achieves a consistent 85% sleep efficiency for two weeks as guided and monitored by the sleep disorder treatment module 220, the user is prompted to lengthen their sleep period gradually. In support of this feature, the sleep disorder treatment module 220 can automatically prompt the user to go to bed 15 minutes earlier every two weeks. The SRT treatment is complete once the user reaches and maintains an 85% sleep efficiency and feels generally refreshed during the day. The user will have then learned how much sleep they need to feel refreshed. Not everyone needs the mythic "eight hours of sleep per night." Some people need more sleep and others need less sleep. The sleep disorder treatment module 220 is designed to accommodate a variety of sleep patterns in a variety of different users.

The sleep disorder treatment module 220 is designed to be used as a sleep maintenance tool as well, even after improvement in sleep patterns is achieved. The sleep disorder treatment module 220 can prompt users to keep daily sleep logs. If the user's sleep efficiency begins to fall, the sleep disorder treatment module 220 can offer another round of SRT or other therapy, starting from the beginning. Also, if a seven hour sleep restriction period does not improve the user's sleep efficiency, the user can be offered a six hour sleep restriction period.

It is important to note that Sleep Restriction Therapy may make the user feel worse before feeling better. This is because the SRT treatment removes the current "sleep coping mechanism" being used, and replaces it with a specified sleep schedule purposely meant to initially cause sleep deprivation. If the user sticks with the SRT treatment program, the sleep deprivation lessens and the user will start sleeping and feeling better. In a particular embodiment, a Rewards Center is provided where the user can redeem points collected for keeping sleep logs or for completing other actions to which incentives are tied. The user can redeem points for prizes, such as animal dream totems, exclusive musical recordings, additional soundscapes, and the like. Additionally, an example embodiment can provide automated information presentations that describe possible sleep diagnoses in more detail, typical diagnostic tests, various treatment options, and the five closest sleep centers to the user's location.

Figure 13:
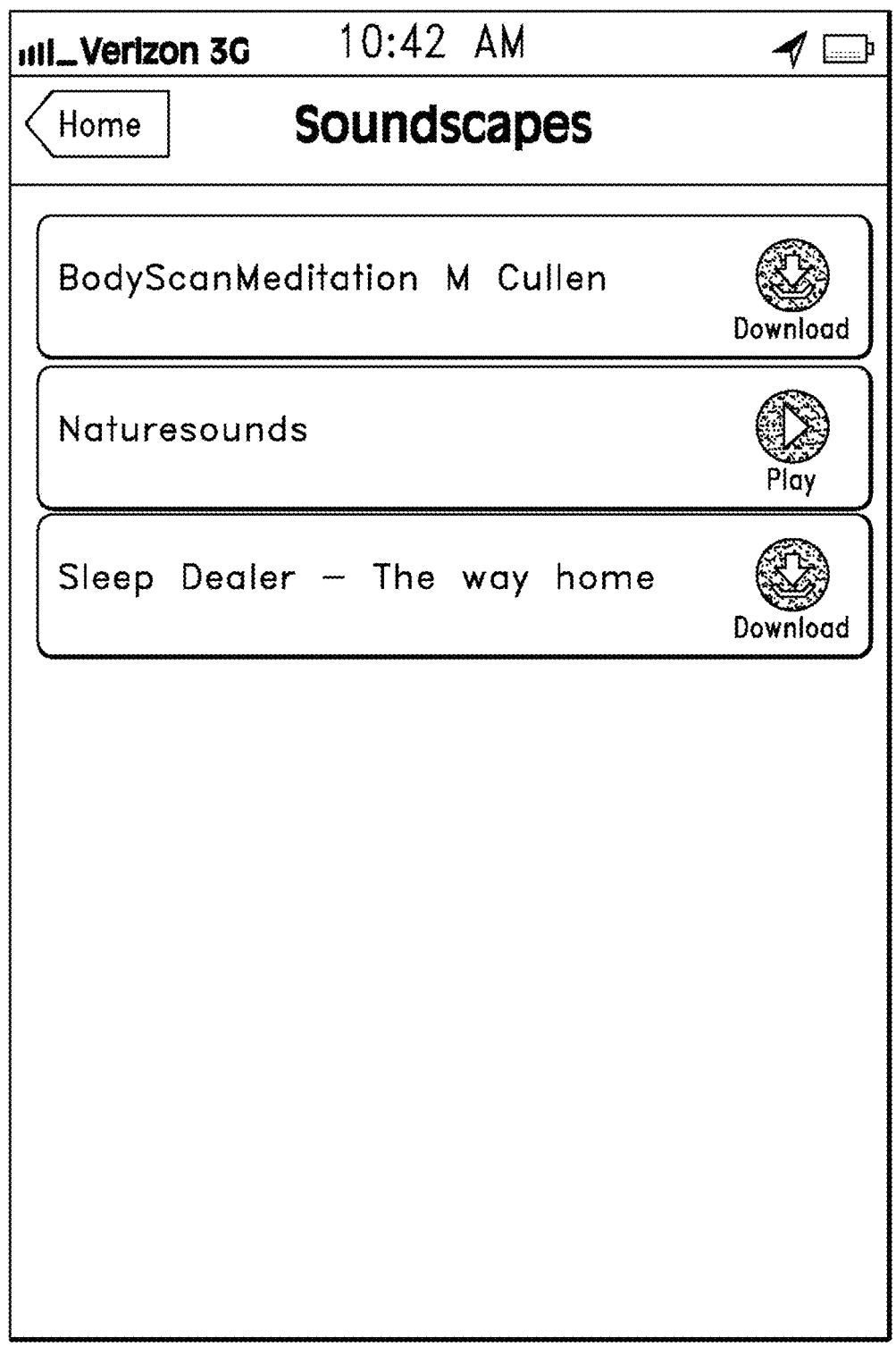
FIG. 13 illustrates an example embodiment, implemented as a mobile app, which shows a soundscape display screen of the user interface of the example embodiment.

FIG. 13 illustrates an example embodiment, implemented as a mobile app, which shows a soundscape display screen of the user interface of the example embodiment. The soundscape display screen offers the user a variety of selectable soundscapes that can be played when the user goes to sleep or awakens. The soundscapes are audio clips of calming sounds and relaxing music, as well as meditations to help the user relax at the beginning or end of their day.

Figure 14:
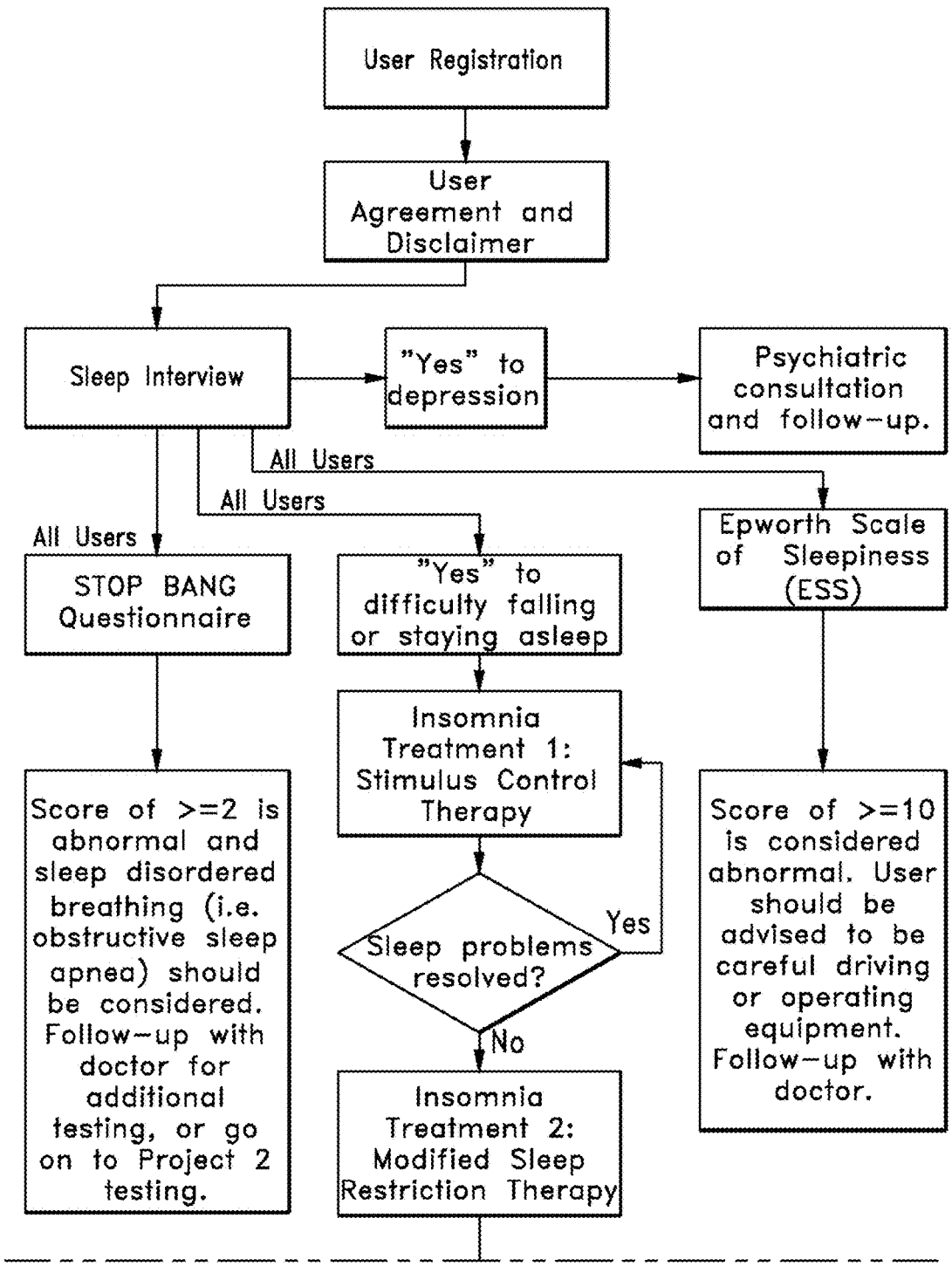
FIGS. 14 through 16 are processing flow charts illustrating an example embodiment of a method as described herein.
Figure 15:
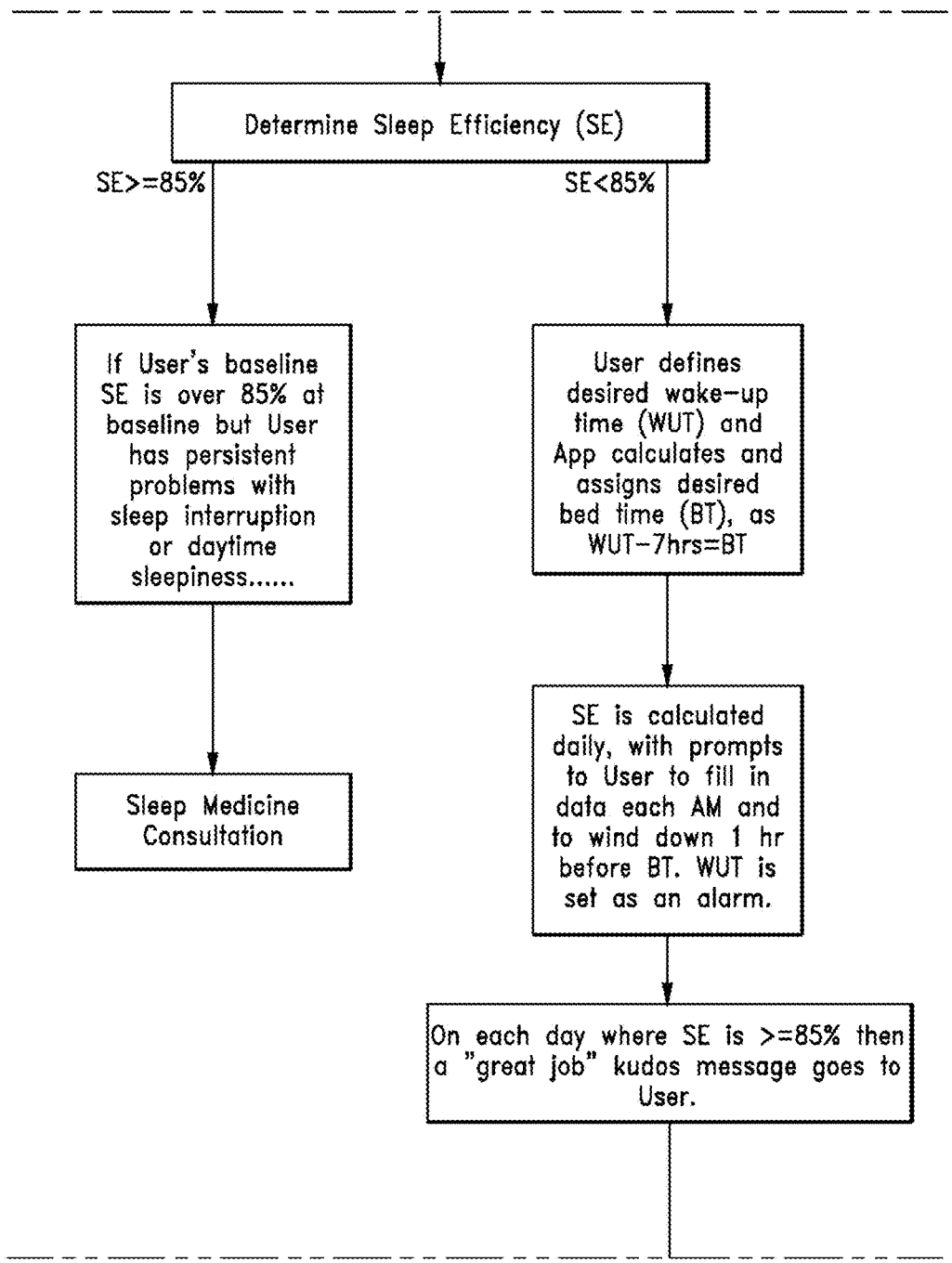
Figure 16:
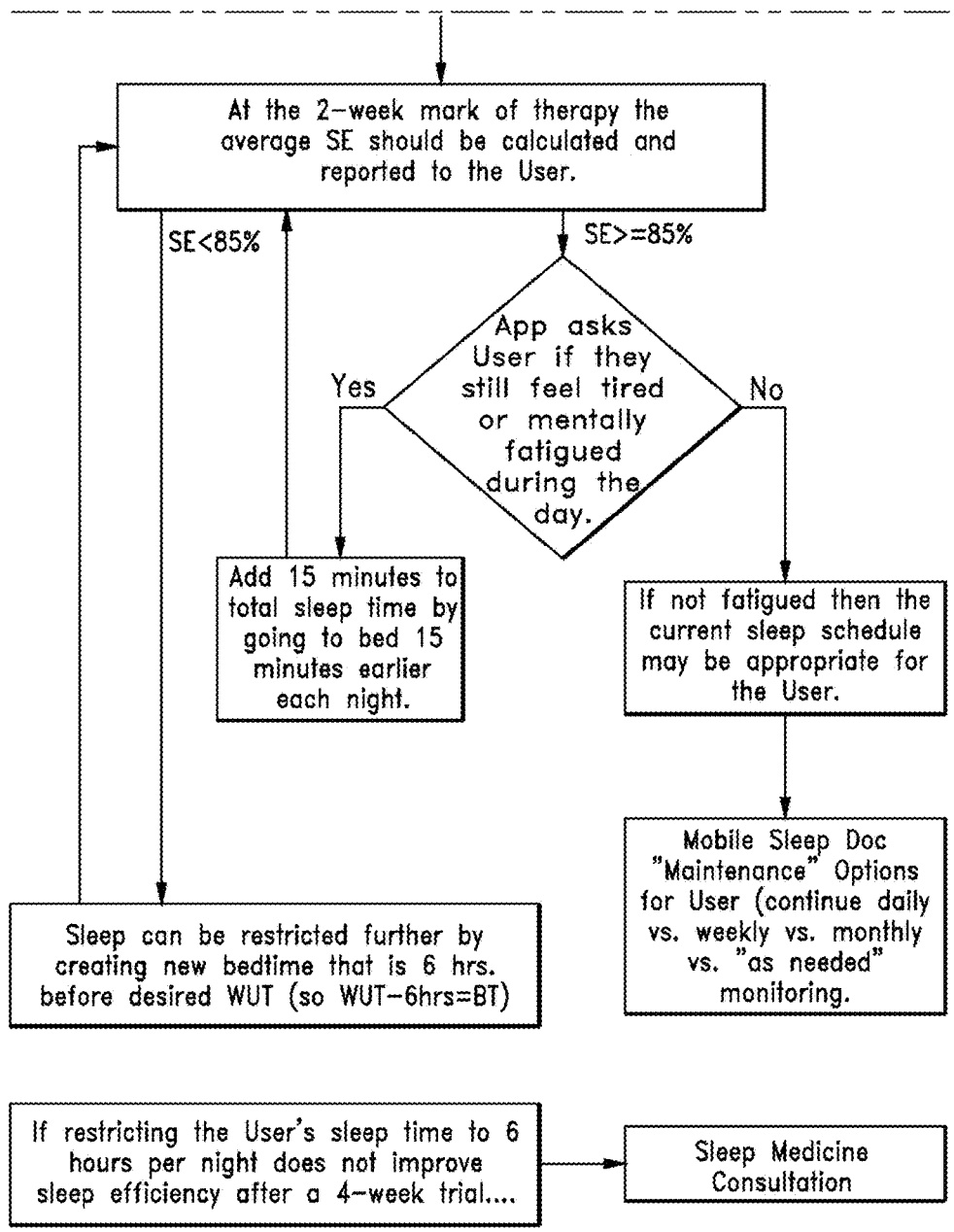

FIGS. 14 through 16 are processing flow charts illustrating an example embodiment of a method as described herein. In the manner described above, the sleep disorder diagnostic module 210 and the sleep disorder treatment module 220 guide the user through a process of sleep disorder diagnostic assessment and sleep disorder treatment options customized for the particular user. As a result, the user achieves improved sleep efficiency.

Referring again to FIGS. 1 and 2, the sleep disorder diagnosis and treatment system 200 of an example embodiment is shown to include a breathing disturbance meter integration module 230. The breathing disturbance meter integration module 230 can be used to detect an OSA condition or other sleep-related condition in a patient. The breathing disturbance meter integration module 230 is in wireless data communication with a breathing disturbance metering system described in more detail below.

Because the vast majority of people with sleep apnea have not yet been diagnosed, two barriers to sleep apnea detection may be the cost and accessibility of testing. After interpreting thousands of sleep studies, both lab and home studies, the inventor herein determined that a patient's sleep apnea can be detected the majority of the time in a single abdominal effort channel, wherein the breathing patterns of a patient are captured by a breathing disturbance metering system.

Figure 17:
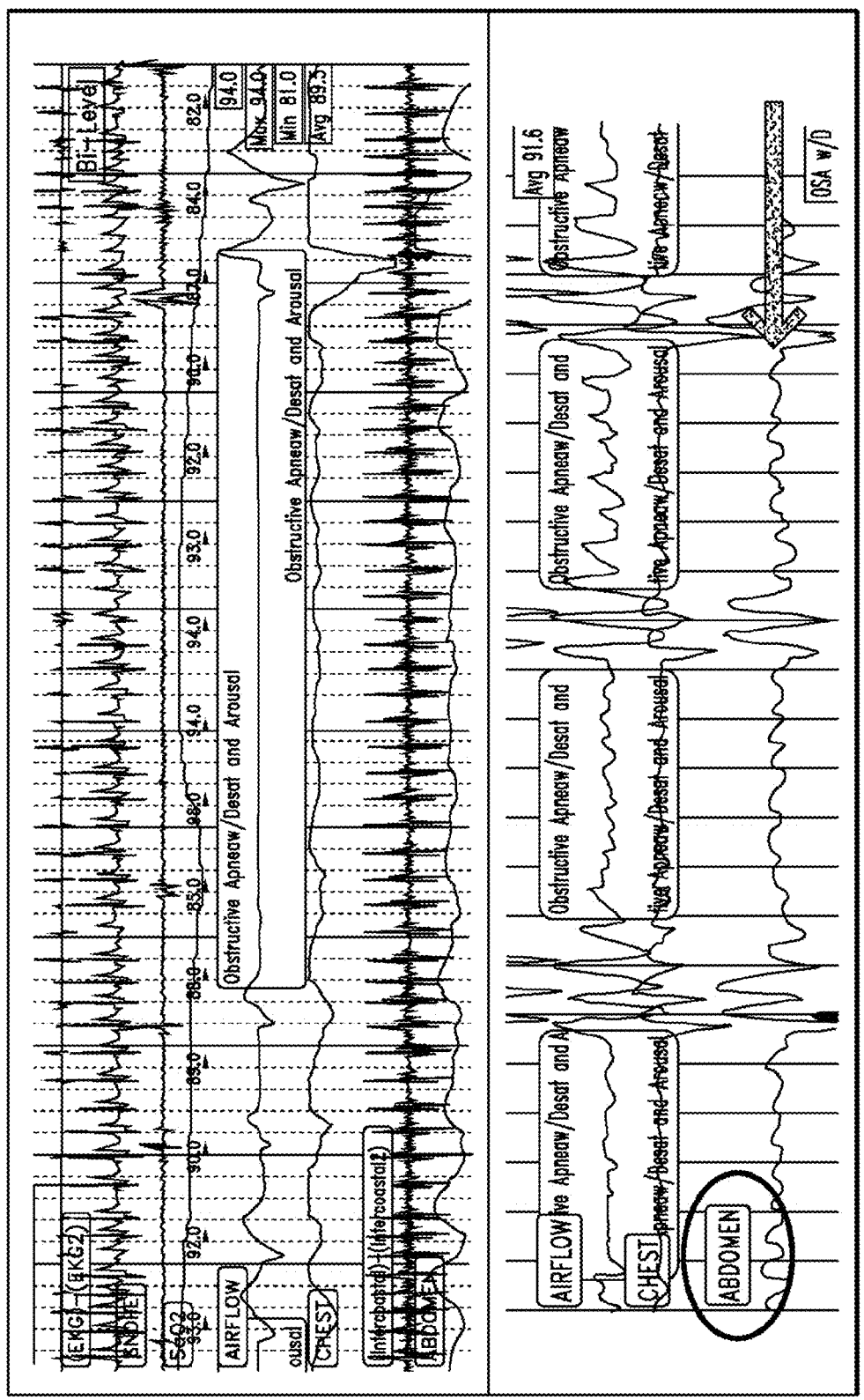
FIGS. 17 and 18 illustrate charts of the breathing patterns of a patient as captured by the breathing disturbance metering system of an example embodiment.
Figure 18:
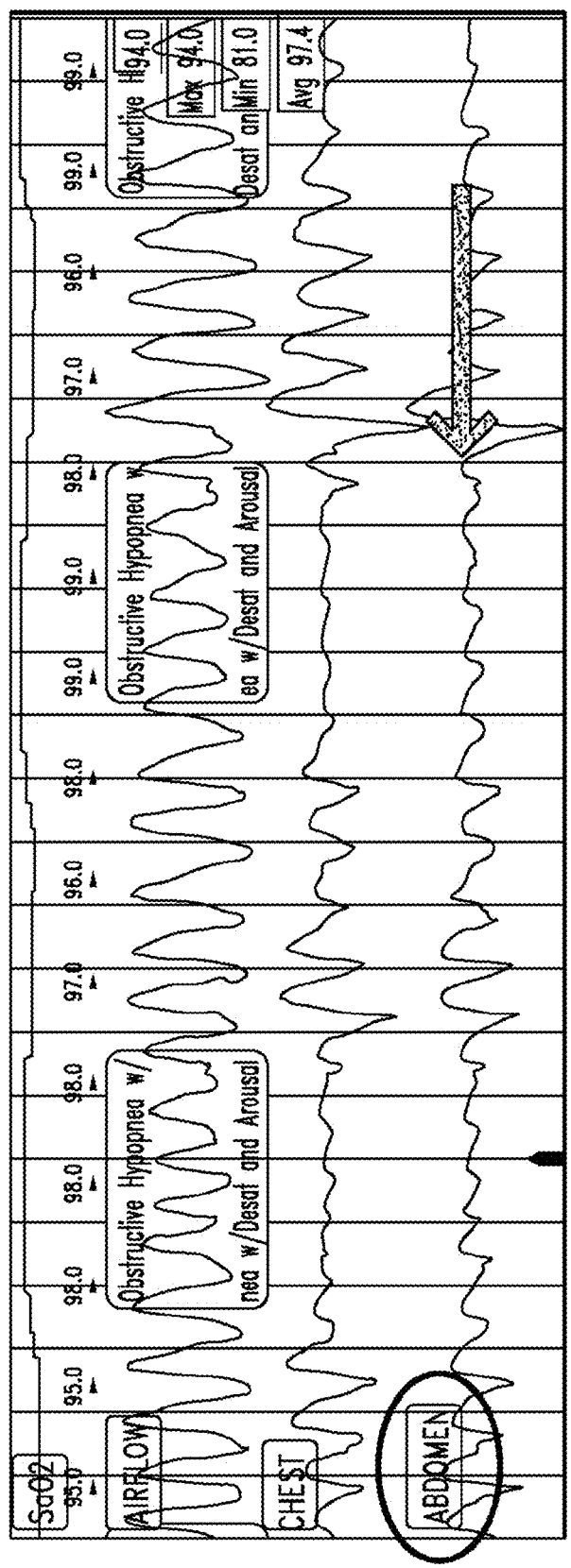

FIGS. 17 and 18 illustrate charts of the breathing patterns of a patient as captured by a breathing disturbance metering system of an example embodiment. As shown in FIG. 17, a sleep apnea condition is a 90% or greater decrease in the breathing airflow of a sleeping person lasting ten seconds or longer. As shown in FIG. 18, a sleep hypopnea condition is a 30% or greater decrease in airflow (from an established baseline) lasting ten seconds or longer. By monitoring the breathing patterns of a sleeping person, the sleep apnea condition and sleep hypopnea condition can be detected. The breathing disturbance metering system and breathing disturbance meter integration module 230 can be used to detect, measure, assess, and respond to the potential OSA conditions present in a patient being monitored. The details of this system in an example embodiment are described below.

Figure 19:
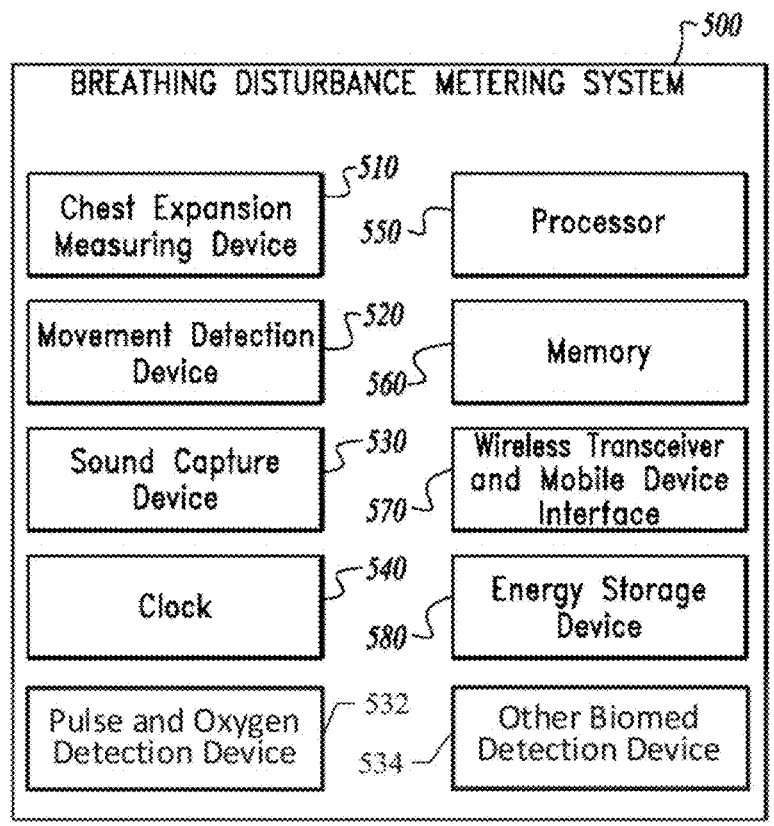
FIG. 19 illustrates an example embodiment of the components of the breathing disturbance metering system of an example embodiment.

FIG. 19 illustrates an example embodiment of the components of the breathing disturbance metering system 500 of an example embodiment. As described herein, the breathing disturbance metering system 500 can also be denoted the sleep metering system or on-body device 500. The breathing disturbance metering system 500 can include a chest expansion measuring device 510 and/or a movement detection device 520. Breathing monitors are well-known in the art. The chest expansion measuring device 510 and/or the movement detection device 520 serve to detect the movements of the chest cavity during the normal breathing cycles of a person. Once the breathing disturbance metering system 500 is calibrated to the normal breathing patterns of a particular individual, the degree of chest cavity movement can correlate to the volume of air respired for each breath. As explained above, anomalies in the breathing patterns of a particular individual can correlate to variations in the degree of chest cavity movement in a series of breaths over a given time period. In an example embodiment, the movement detection device 520 can include a level that can measure degrees of movement up and down or side to side.

These variations in breathing patterns can be aggregated into a breathing disturbance index (BDI). Because the breathing disturbance metering system is not measuring airflow, we derived new terminology to guide the development of a device able to measure abnormalities of one's breathing pattern based on abdominal movements. Respiratory effort reduction events, or RERE's, are defined as a >=30% reduction in amplitude of a preceding abdominal effort waveform, lasting 10 seconds or longer or compared to a running baseline over a pre-defined timeframe. A respiratory effort exaggeration event (REEE) is an increase in a respiratory waveform of 150% to 400% over baseline. A REEE is not counted if immediately adjacent to a RERE to avoid double scoring the same event. A RERE that is 10-29% reduced from baseline but accompanied by a >=3% fall in $O^2$ saturation is counted as an event. In general, the BDI for a particular subject can be determined from the general equation: BDI=#RERE's+#REEE's/total recording time in hours. Segments of data artifacts are identified and removed from the equation.

In the example embodiment, the BDI can be computed as follows:

$$BDI = \frac{\#RERE's + \#REEE's}{\#hours\ of\ testing/recording\ time}$$

In an example embodiment, the breathing disturbance metering system 500 can use clock 540 to measure a start and stop time. Initially, the user can press a button on the device 500 to activate the device 500 when they retire to the bed. In the morning, the user can press a button to deactivate the device 500 after they wake up. After activation, the breathing disturbance metering system 500 can sample the user's breathing patterns over pre-configured time periods (sampling period). For example, the breathing disturbance metering system 500 can be configured to sample the user's chest cavity movement (i.e., breathing pattern) for a five minute sampling period. During this sampling time period, the breathing disturbance metering system 500 can record the user's breathing patterns and save this data in the memory 560. At the end of the five minute sampling period, the breathing disturbance metering system 500 can enter a low power mode (rest period) to save power. At a configurable time later (e.g., 15 minutes), the breathing disturbance metering system 500 can start a new five minute sampling period during which a new set of breathing pattern data is gathered and retained in memory 560. Each set of breathing pattern data is time stamped with the current or relative time/date. In this manner, the breathing disturbance metering system 500 can gather breathing pattern data for the user over the entire night. As the breathing pattern data for a particular user is gathered, the breathing disturbance metering system 500 can use the processor 550 to scan the data for patterns consistent with apnea or hypopnea conditions. The processor 550 can score any detected respiratory effort reduction or exaggeration condition (e.g., RERE or REEE) for a level of severity. The respiratory effort detection data and related scoring can also be stored in the memory 560. It will be apparent to those of ordinary skill in the art that a variety of related data can also be generated and retained. It will also be apparent to those of ordinary skill in the art that different sampling periods and/or rest periods can be used for a particular embodiment. Periodically throughout the night or the following morning, the breathing disturbance metering system 500 can establish wireless data communications with the breathing disturbance meter integration module 230 and upload the data saved in memory 560 to a memory in the user platform 140. A wireless transceiver and mobile device interface 570 is provided in the breathing disturbance metering system 500 to enable this data communication. An energy storage device (e.g., a battery) 580 is provided in the breathing disturbance metering system 500 to power the system. In a particular embodiment, a sound capture device (e.g., a microphone) 530 can be used to record the sounds made by the user during a sleep cycle. These sounds can include snoring, which can also be an indicator disrupted sleep. For example, a decibel variation in a periodic manner can be consistent with sleep disordered breathing. In this manner, the sleep disorder diagnosis and treatment system 200 of an example embodiment can obtain real-time data related to the sleeping patterns of a user and data related to potential OSA conditions present in a patient being monitored.

Figure 20:
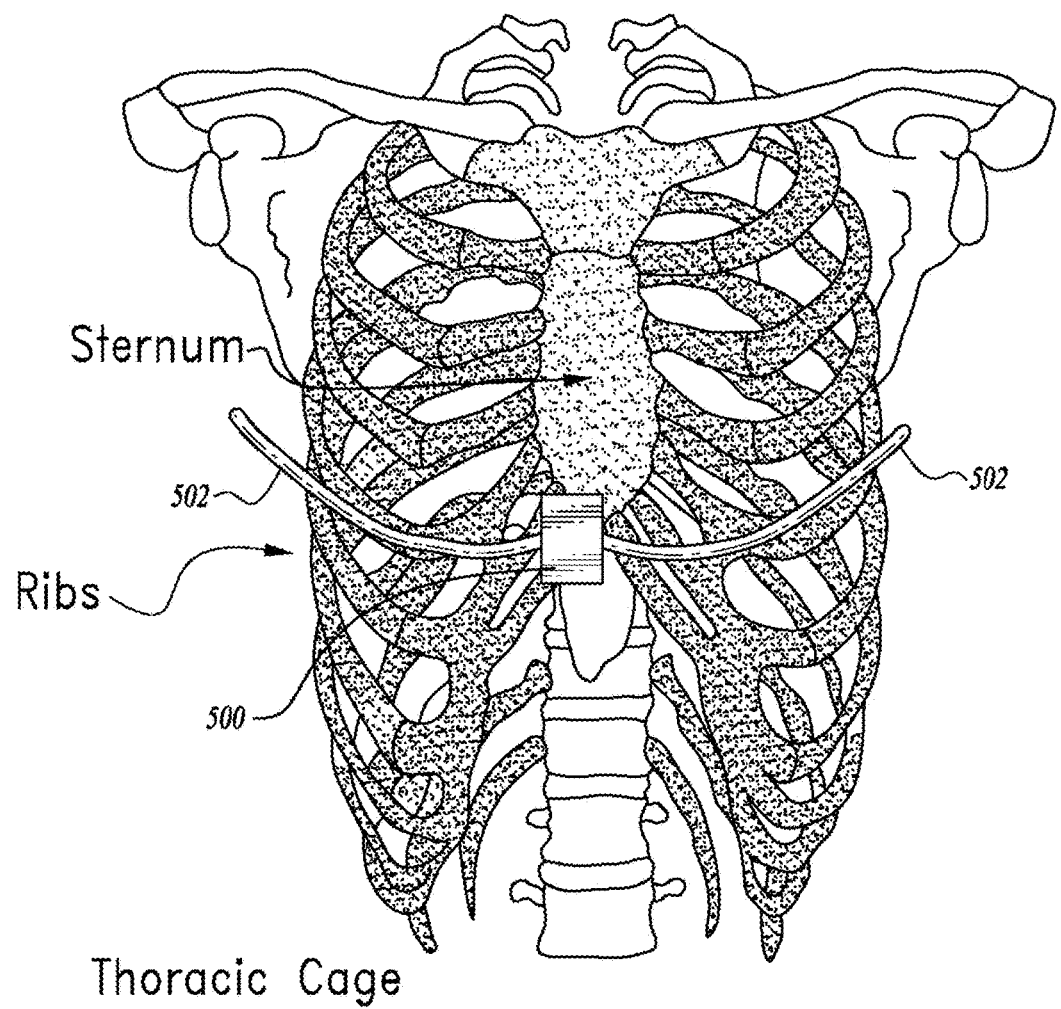
FIG. 20 illustrates the thoracic cage of a human and the relative placement of the breathing disturbance metering system of an example embodiment.
Figure 21:
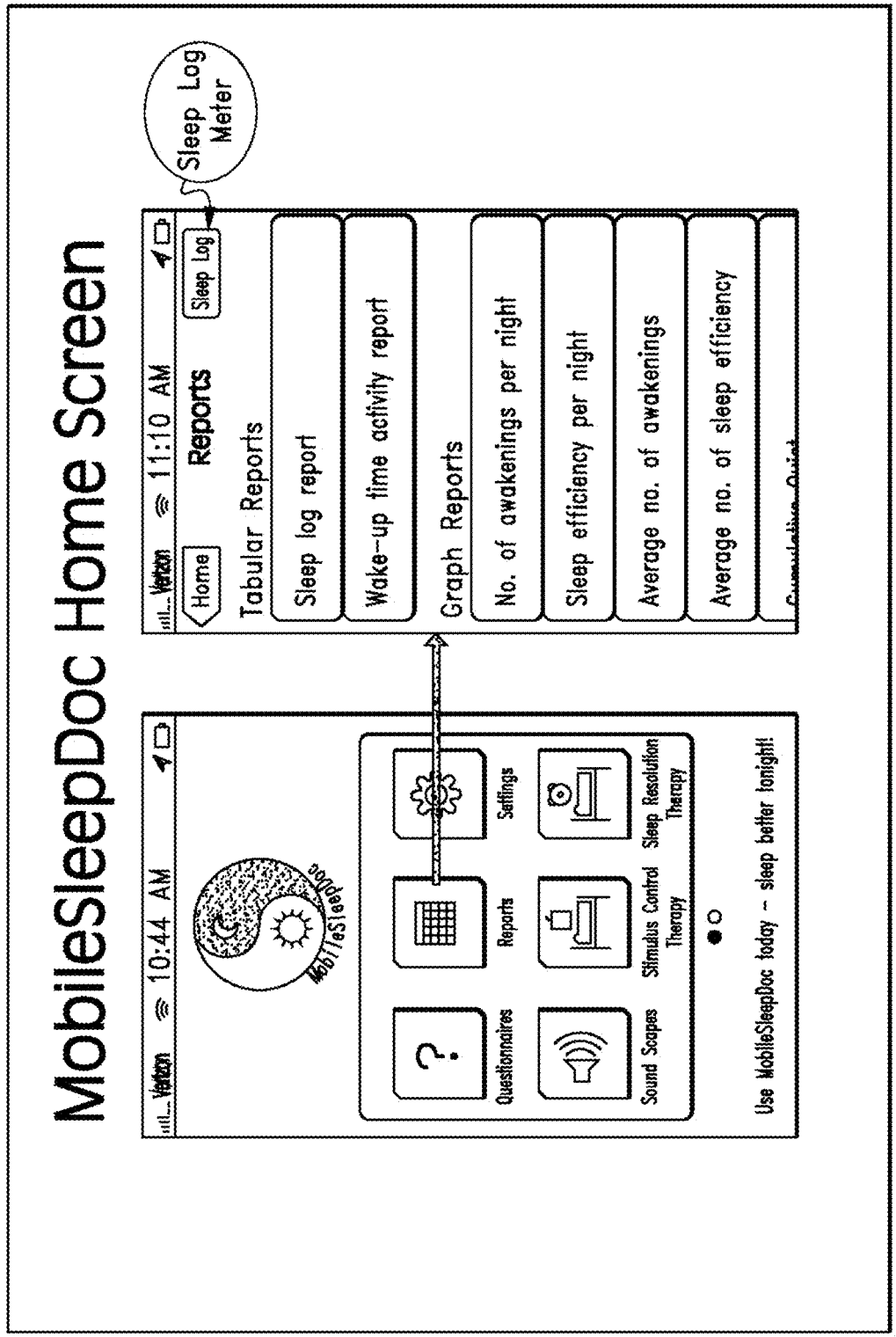
Figure 23:
Figure 24:
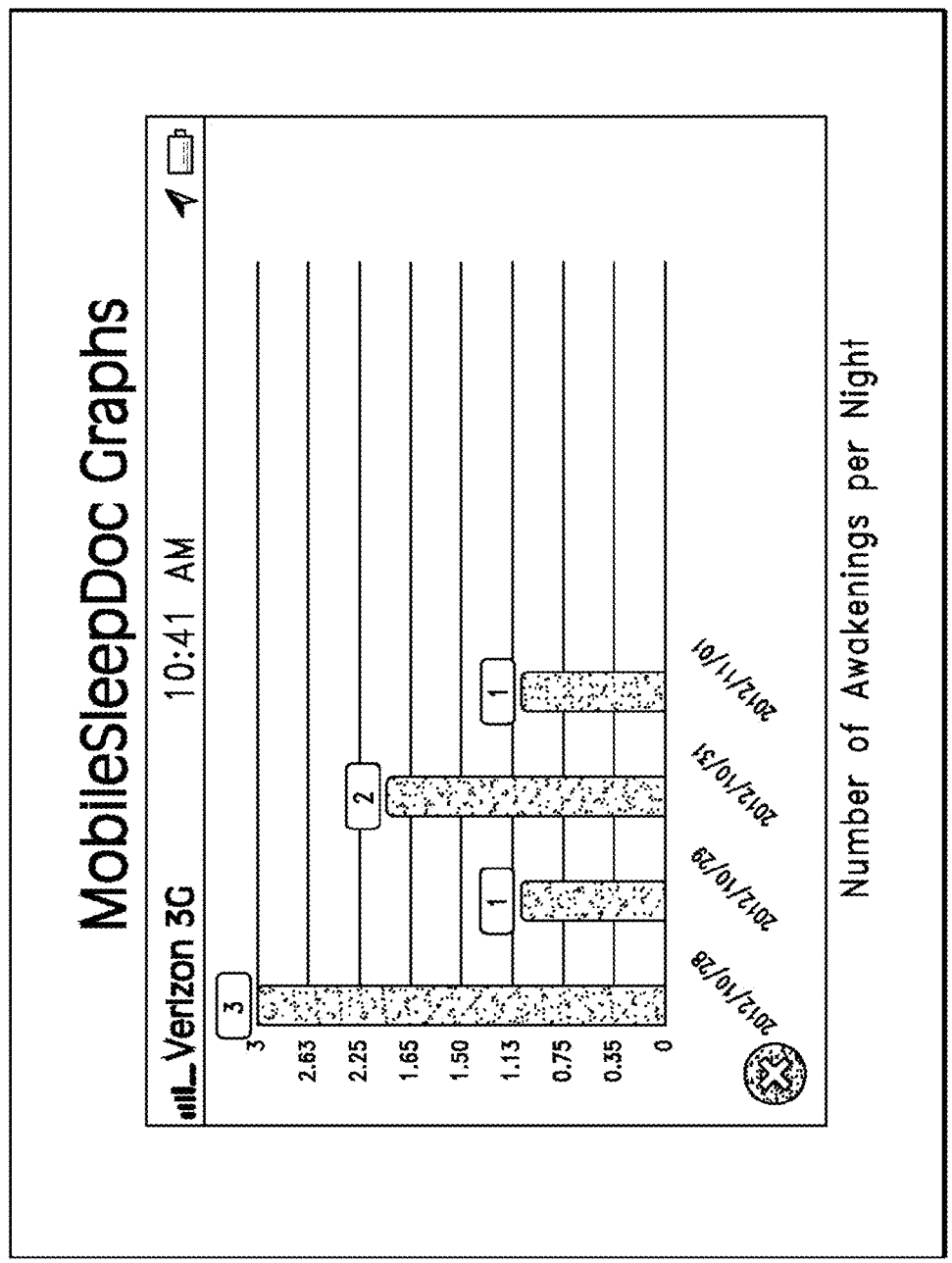
Figure 25:
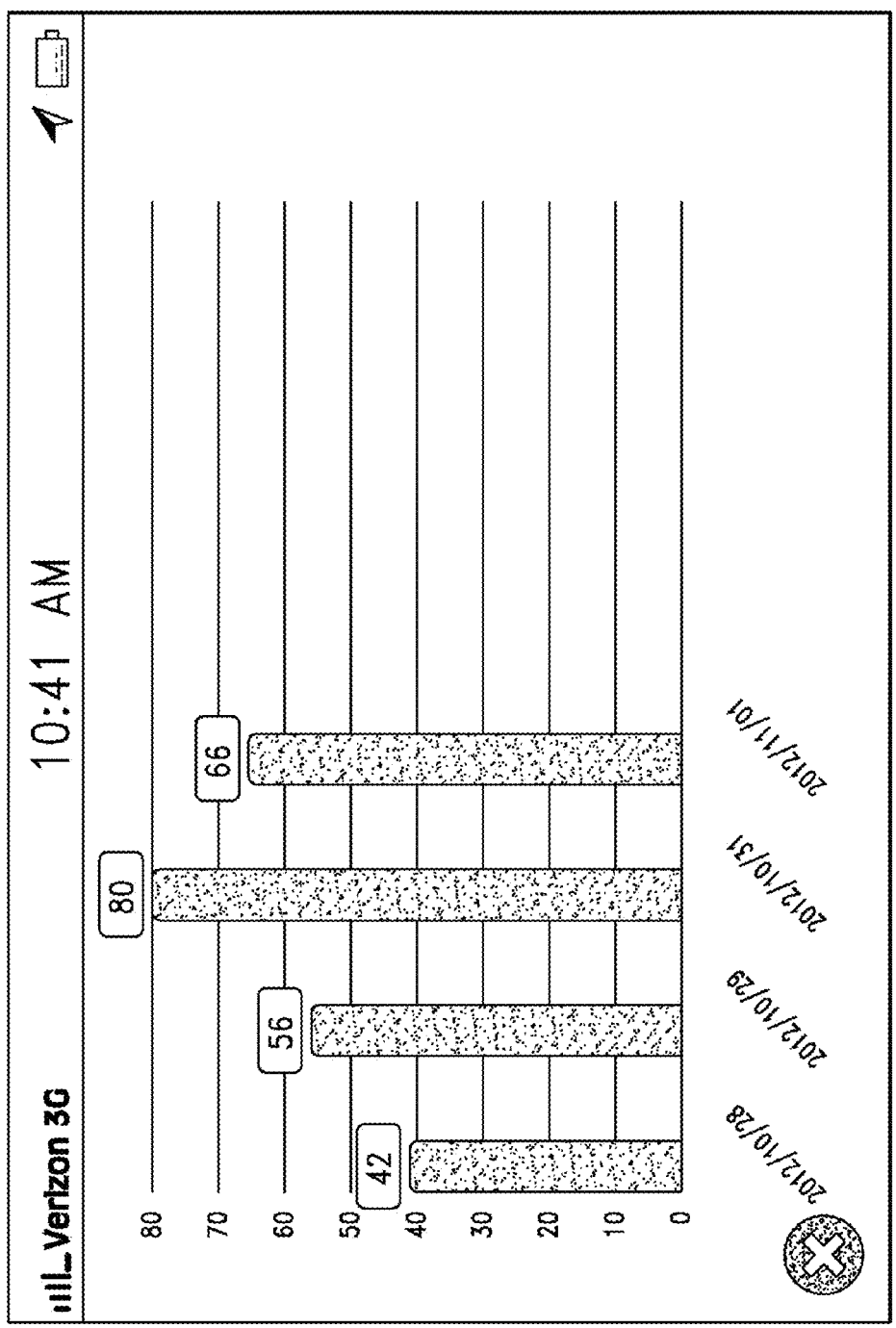

FIG. 20 illustrates the thoracic cage of a human and the relative placement of the breathing disturbance metering system 500 of an example embodiment. As shown in FIG. 20, the breathing disturbance metering system 500 can be positioned for data recording at the top of the user's abdomen with the top of the device positioned at the bottom of the user's sternum. The breathing disturbance metering system 500 can be held in place with a belt or straps 502.

Referring again to FIGS. 1 and 2, the sleep disorder diagnosis and treatment system 200 of an example embodiment is shown to include a reports module 240. The reports module 240 can be used to present information to a user in the form of tabular or graphical reports. FIGS. 21 through 25 illustrate an example embodiment, implemented as a mobile app, which shows various report display screens of the user interface of the example embodiment. In support of a variety of tabular reports, the reports module 240 can present a Sleep Log Report showing a list of nightly summaries of information from the user's sleep logs, such as the time the user went to sleep, total number of awakenings during the night, and how long the user slept. The Activity Report shows a list of nightly details about nighttime awakenings, such as why the user woke up and how long the user was awake.

In support of a variety of graphical reports, the reports module 240 can present several report formats in the form of graphs. For example, the user can look at the number of awakenings and sleep efficiency on a nightly basis. The user can also look at the average number of awakenings and average sleep efficiency over a specified period of time. This allows the user to look at detailed nightly data, as well as trends, and determine whether or not progress is being made in a sleep disorder treatment program.

Referring again to FIGS. 1 and 2, the sleep disorder diagnosis and treatment system 200 of an example embodiment is also shown to include a user account management module 250. The user account management module 250 can be used to create and maintain a user account with the sleep disorder diagnosis and treatment system 200. The user account management module 250 can also be used to configure user settings, create and maintain a user/user profile, and otherwise manage user data and operational parameters for the sleep disorder diagnosis and treatment system 200. In the example embodiment described herein, a user can register as an identified and authenticated user in order to interact with system 200 and receive sleep disorder diagnosis and treatment. The registered user can enter their name, email address, and other personal information. Once this information is entered, a user account is created and the user can interact with system 200 and receive sleep disorder diagnosis and treatment.

Referring again to FIGS. 1 and 2, the sleep disorder diagnosis and treatment system 200 of an example embodiment is shown to include an administrative management module 260. The administrative management module 260 can be used by an agent of the sleep disorder diagnosis and treatment system 200 to manage user accounts and to manage the sleep disorder diagnosis and treatment system. The administrative management module 260 can also be used to enforce privacy protections and content controls for users. Moreover, the administrative management module 260 can also be used to generate and/or process a variety of analytics associated with the operation of the sleep disorder diagnosis and treatment system 200. For example, the administrative management module 260 can generate various statistical models that represent the activity of the community of users and related diagnoses and treatments. These analytics can be shared, licensed, or sold to others under strict privacy protections and/or as data that has been processed to remove personal user information.

Although the various user interface displays provided by the example embodiments described herein are nearly infinitely varied, several sample user interface displays and sequences are provided herein and in the corresponding figures to describe various features of the disclosed embodiments. These sample user interface displays and sequences are described herein and in the accompanying figures. It will be apparent to those of ordinary skill in the art that equivalent user interface displays and sequences can be implemented within the scope of the inventive subject matter disclosed and claimed herein.

Figure 26:
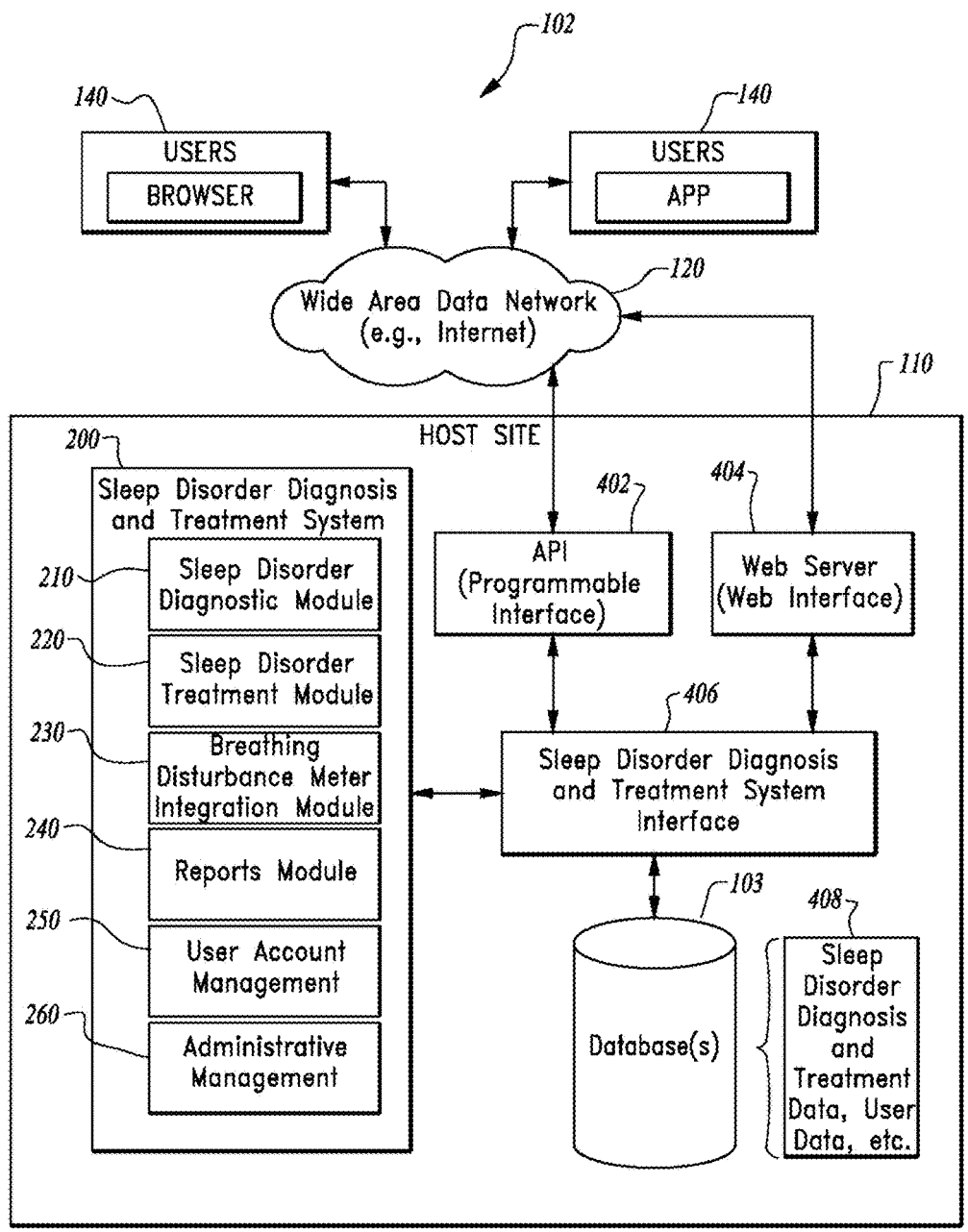
FIG. 26 illustrates another example embodiment of a networked system in which various embodiments may operate.

Referring now to FIG. 26, another example embodiment 102 of a networked system in which various embodiments may operate is illustrated. In the embodiment illustrated, the host site 110 is shown to include the sleep disorder diagnosis and treatment system 200. The sleep disorder diagnosis and treatment system 200 is shown to include the functional components 210 through 260, as described above. In a particular embodiment, the host site 110 may also include a web server 404, having a web interface with which users may interact with the host site 110 via a user interface or web interface. The host site 110 may also include an application programming interface (API) 402 with which the host site 110 may interact with other network entities on a programmatic or automated data transfer level. The API 402 and web interface 404 may be configured to interact with the sleep disorder diagnosis and treatment system 200 either directly or via an interface 406. The sleep disorder diagnosis and treatment system 200 may be configured to access a data storage device 103 and data 408 therein either directly or via the interface 406.

Figure 27:
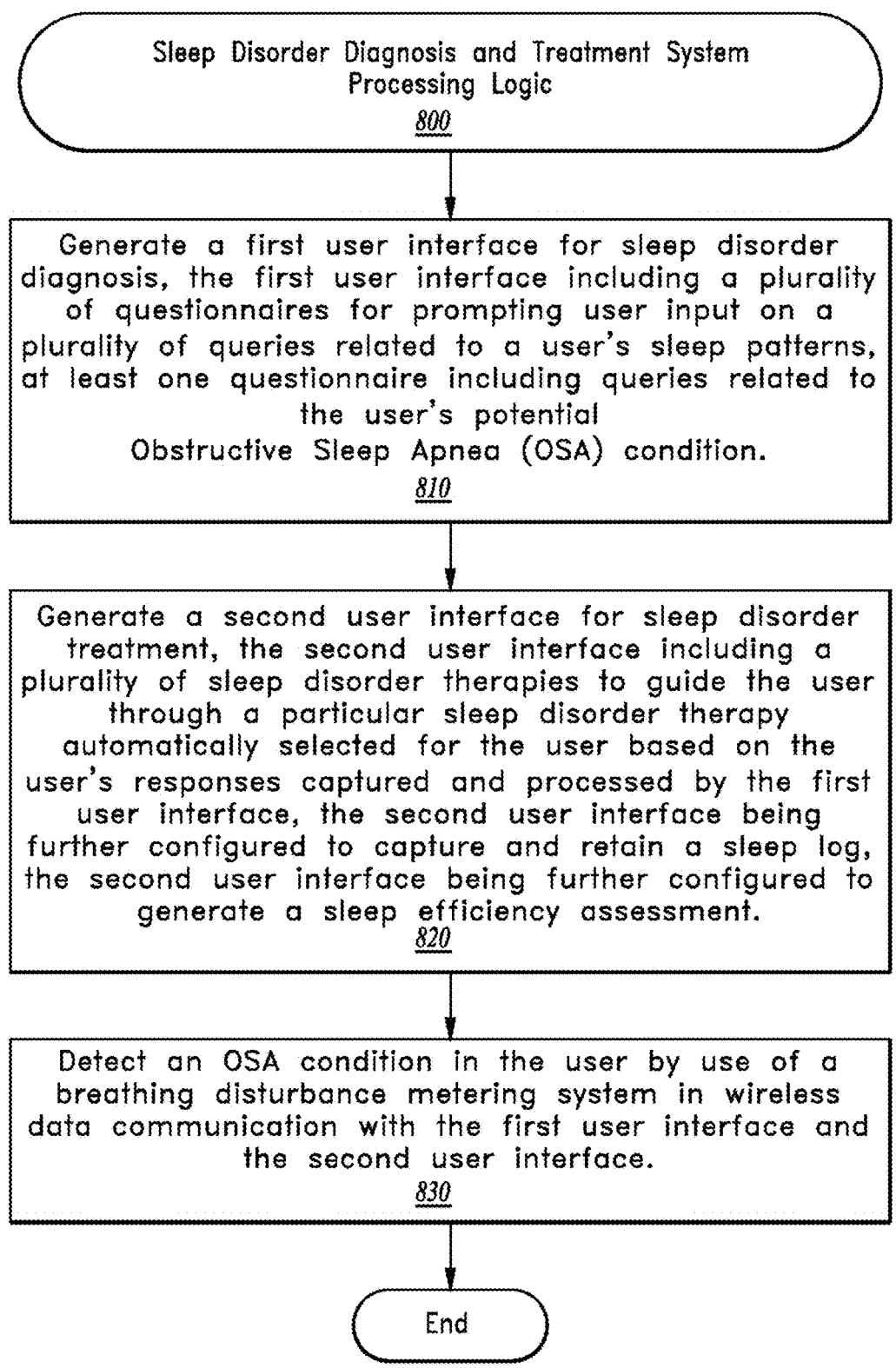
FIG. 27 is a processing flow chart illustrating an example embodiment of a method as described herein.

Referring now to FIG. 27, a processing flow diagram illustrates an example embodiment of a sleep disorder diagnosis and treatment system 200 as described herein. The system 800 of an example embodiment is configured to: generate a first user interface for sleep disorder diagnosis, the first user interface including a plurality of questionnaires for prompting user input on a plurality of queries related to a user's sleep patterns, at least one questionnaire including queries related to the user's potential Obstructive Sleep Apnea (OSA) condition (processing block 810); generate a second user interface for sleep disorder treatment, the second user interface including a plurality of sleep disorder therapies to guide the user through a particular sleep disorder therapy automatically selected for the user based on the user's responses captured and processed by the first user interface, the second user interface being further configured to capture and retain a sleep log, the second user interface being further configured to generate a sleep efficiency assessment (processing block 820); and detect an OSA condition in the user by use of a breathing disturbance metering system in wireless data communication with the first user interface and the second user interface (processing block 830).

Figure 28:
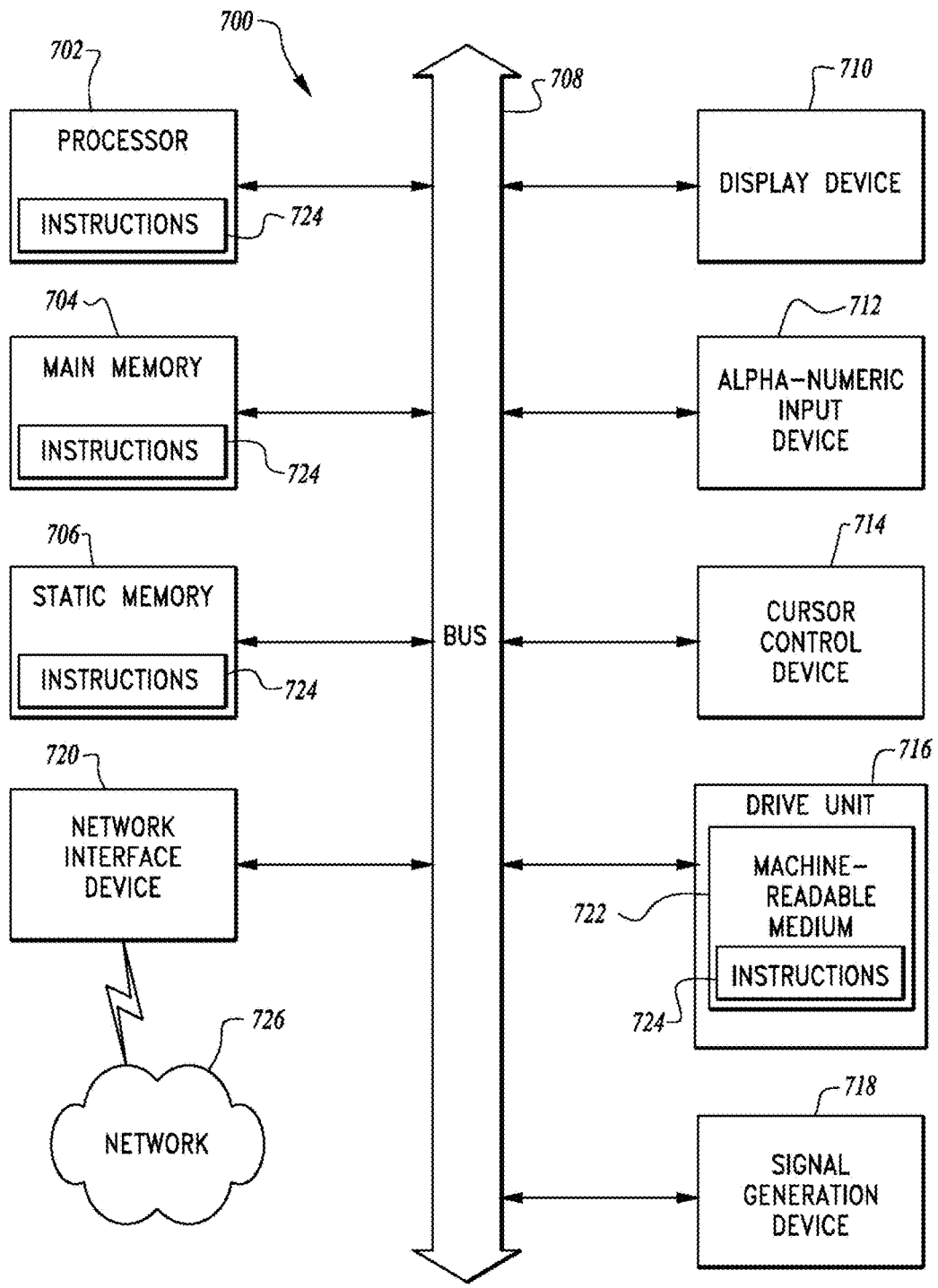
FIG. 28 shows a diagrammatic representation of machine in the example form of a computer system within which a set of instructions when executed may cause the machine to perform any one or more of the methodologies discussed herein.

FIG. 28 shows a diagrammatic representation of a machine in the example form of a computer system 700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 700 includes a data processor 702 (e.g., a central processing unit (CPU), a graphics processing unit (GPU), or both), a main memory 704 and a static memory 706, which communicate with each other via a bus 708. The computer system 700 may further include a display unit 710 (e.g., a liquid crystal display (LCD), plasma, or a cathode ray tube (CRT)). The computer system 700 also includes an input device 712 (e.g., a keyboard), a cursor control device 714 (e.g., a computer mouse or trackpad), a disk drive unit 716, a signal generation device 718, and a network interface device 720.

The disk drive unit 716 includes a machine-readable medium 722 on which is stored one or more sets of instructions (e.g., software 724) embodying any one or more of the methodologies or functions described herein. The instructions 724 may also reside, completely or at least partially, within the main memory 704, the static memory 706, and/or within the processor 702 during execution thereof by the computer system 700. The main memory 704 and the processor 702 also may constitute machine-readable media. The instructions 724 may further be transmitted or received over a network 726 via the network interface device 720. While the machine-readable medium 722 is shown in an example embodiment to be a single medium, the term "machine-readable medium" should be taken to include a single non-transitory medium or multiple non-transitory media (e.g., a centralized or distributed database, and/or associated caches and servers) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

Figure 29:
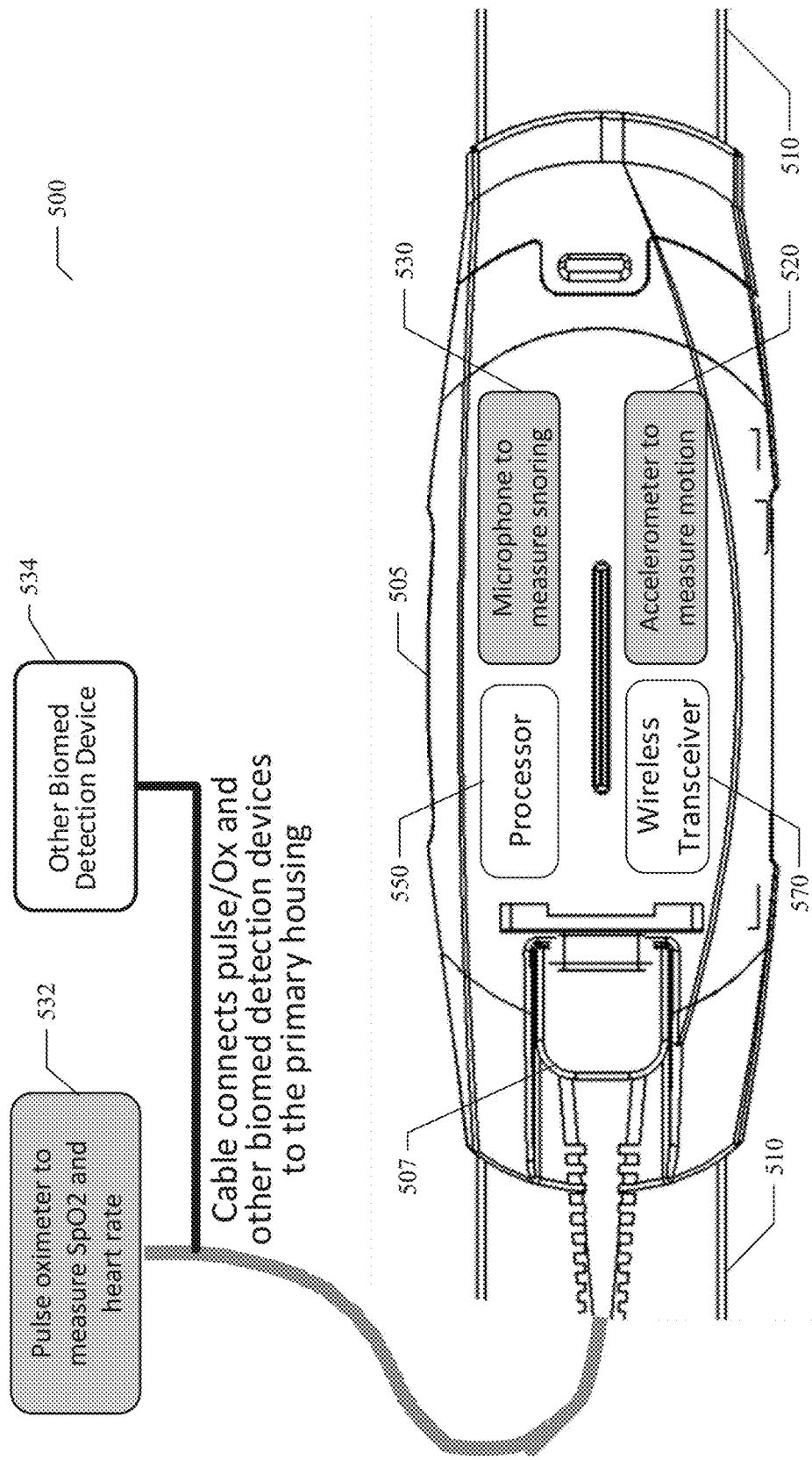
FIG. 29 illustrates an example embodiment of the components of the sleep metering system of an example embodiment.

FIG. 29 illustrates an example embodiment of the components of the sleep metering system 500 of an example embodiment. As shown, an example embodiment can include a housing 505 to contain an array of sensors for detecting various conditions and events in a human subject wearing the sleep metering system 500 around their chest. The housing 505 is configured in an elongated low profile design to minimize the discomfort of a subject wearing the sleep metering system 500 during sleep. A belt or strap 510 is coupled to the housing 505 in a loop to enable the sleep metering system 500 to be attached to the chest of a subject while the subject is sleeping. The housing 505 of the sleep metering system 500 is configured to include an array of sensors including: an accelerometer, gyroscope, or other motion detection device 520 to detect and measure movement and body position of the subject wearing the sleep metering system 500; and a microphone or other sound detection device to detect and measure a sound level or snoring event of the subject wearing the sleep metering system 500. The housing 505 of the sleep metering system 500 is also configured with an electrical connector 507 to provide an electrical/data interface with additional sensors of the array of sensors. In an example embodiment, the additional sensors coupled to the housing 505 via connector 507 can include: a pulse oximeter device 532 to detect and measure a level of arterial oxygen saturation (SpO2) in the blood and the heart rate of the subject wearing the sleep metering system 500; and other biomedical devices 534 to detect and measure other conditions and events (e.g., temperature, pressure, chemical or acidity concentration, blood viscosity, biological magnetic field, galvanic skin response (GSR), wireless interfaces to implanted electromechanical devices, pacemakers, implanted insulin pumps, and the like) in a subject wearing the sleep metering system 500.

FIGS. 30 and 31 illustrate an example embodiment of the inductive belt component of the sleep metering system 500 of an example embodiment. The additional sensors of the array of sensors of the sleep metering system 500 can also include a chest expansion measuring device or a device to measure respiratory effort 510. In an example embodiment, an inductive belt attached to the housing 505 is provided for this purpose. The respiratory effort detection device 510 can be used to detect and measure airflow and respiratory effort in the subject. The raw sensor data from each of these sensors of the sensor array can be transferred to a processor 550 of the sleep metering system 500. The processor 550 can pre-process the raw sensor data (e.g., filter, sequence, timestamp, normalize, packetize, etc.) for subsequent transfer to a central server 110 via the wireless transceiver 570. The pre-processing performed by the processor 550 can also include signal processing to remove undesirable noise from the raw sensor data. The pre-processing performed by the processor 550 can also include filters to reject or remove invalid sensor data that may be received when the sleep metering system 500 is detached from the subject or when the subject is awake and not ready to activate the sensor data recording and processing functions of the sleep metering system 500.

Figure 32:
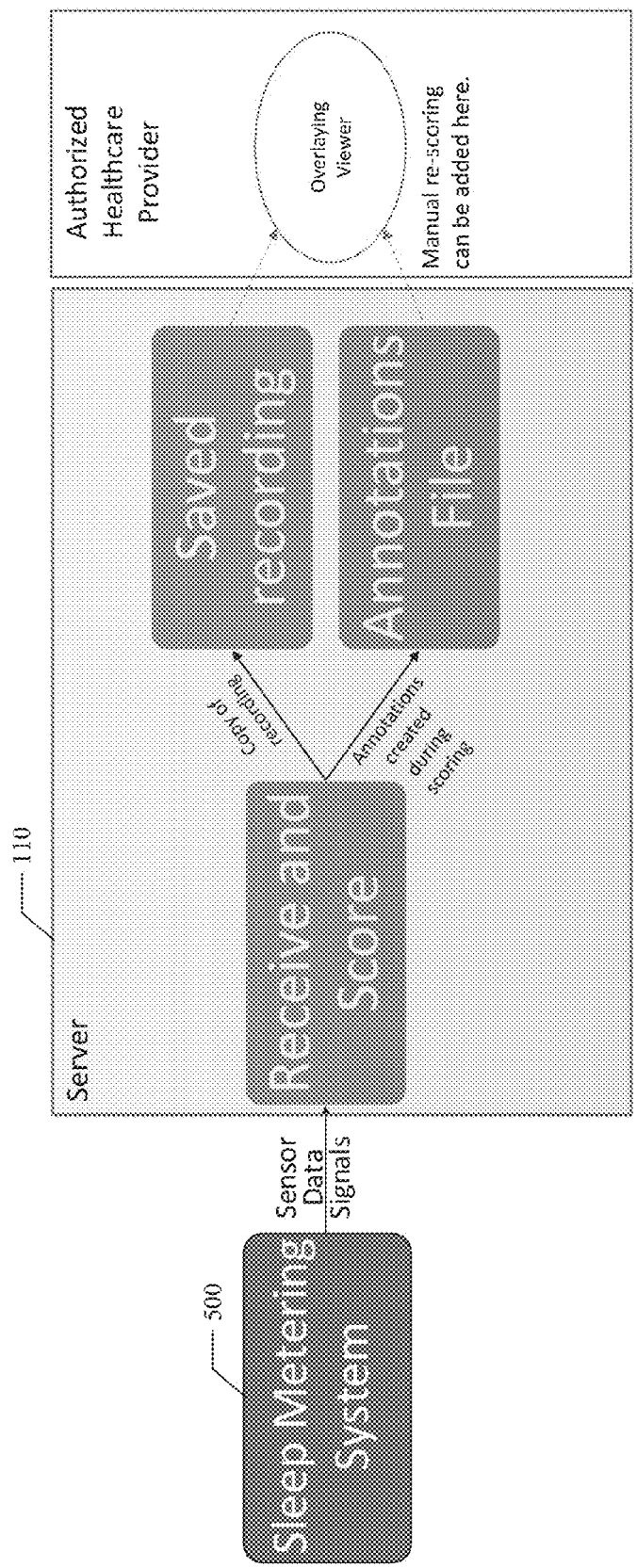
FIGS. 32 and 33 illustrate an example embodiment of the flow of sensor data signals and processed sensor data from the sleep metering system to a networked server for further processing and scoring and for networked access by authorized healthcare providers.
Figure 33:
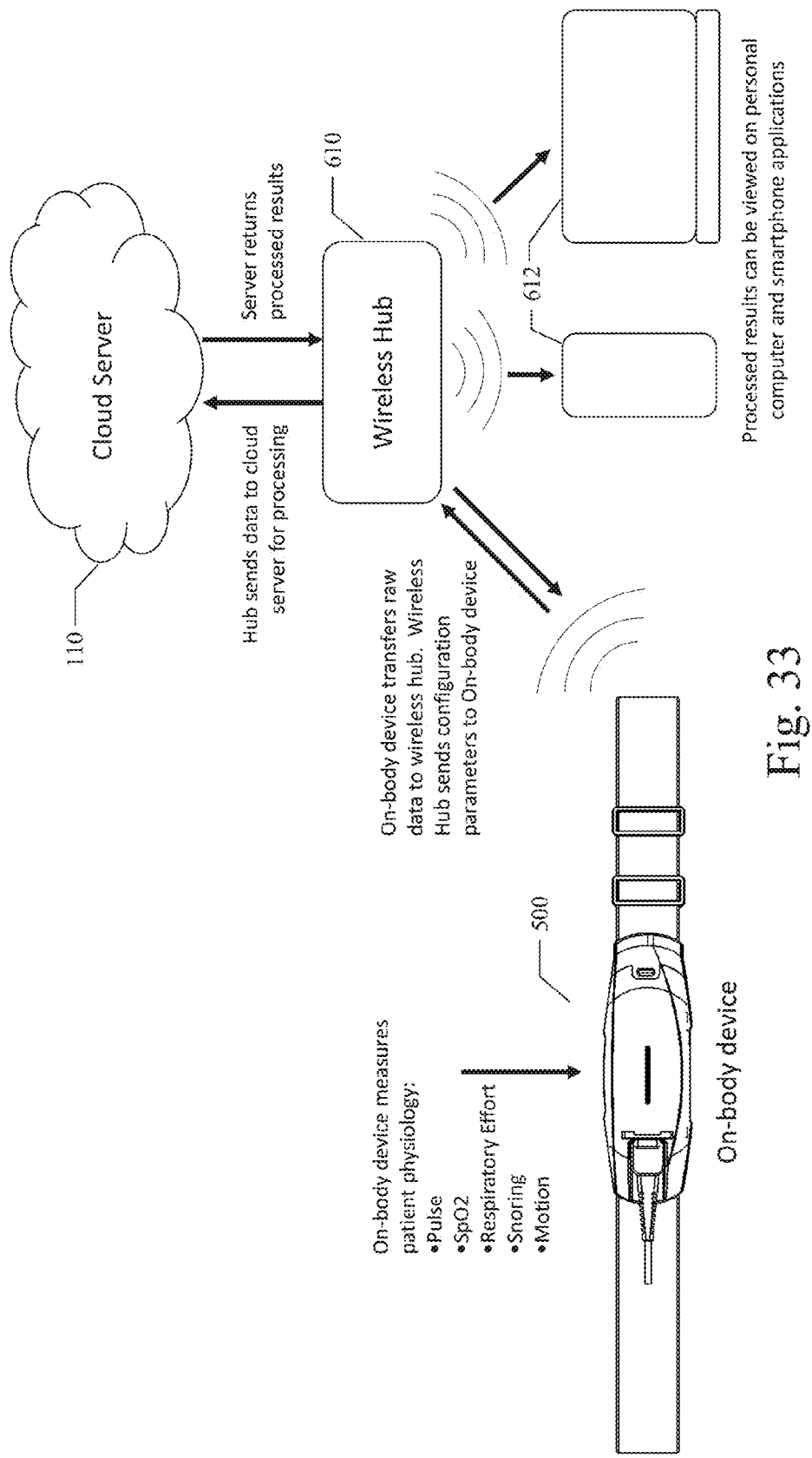

FIGS. 32 and 33 illustrate an example embodiment of the flow of pre-processed sensor data signals and processed sensor data from the sleep metering system 500 to a networked server 110 for further processing and scoring and for networked access by authorized healthcare providers. As shown in FIGS. 32 and 33, the sleep metering system 500 being worn by a subject (e.g., on-body device 500) can capture and pre-process a variety of sensor data from the sensor array of the sleep metering system 500. For example as described above, the sleep metering system 500 can detect, measure, and transmit pulse data, SpO2, respiratory effort data, breathing pattern data, airflow data, snoring data, motion data, body position data, and other biomedical metrics and sensor data obtained from a subject wearing the sleep metering system 500. This sensor data can be preprocessed by the sleep metering system 500 in the manner described above. Additionally, portions of the sensor data or combinations of the sensor data can be arranged into data channels for scoring, which can be configured for display in charts or graphs as shown for several examples in FIGS. 34 through 39 and described below.

Referring still to FIGS. 32 and 33, the sleep metering system 500 can periodically or upon request transfer blocks of the sensor data to a central server (cloud server) 110 via a wireless data connection and network 120. As shown in FIG. 33, the sleep metering system 500 can also send the sensor data via a wireless hub 610, which can forward the sensor data to the central server 110 for further processing and scoring. The scoring of the sensor data by the server 110 is described in detail above. The server 110 can also record the received sensor data to maintain a time-stamped historical record or recording of the received sensor data. The sensor data can also be annotated with metadata, such as timestamps, subject identification or demographic data, etc. The scored, recorded, and annotated sensor data for the particular subject (e.g., the subject's sleep data) can be maintained and stored in a cloud data storage device 103. The subject's sleep data can be anonymized to remove specific identifying information related to the particular subject and thereby make the retention and accessibility of the sleep data compliant with the Health Insurance Portability and Accountability Act of 1996 ("HIPAA"). Given the implementation of a sufficient level of data access security, the sleep data can be made accessible to authorized healthcare providers via a secure data network connection as shown in FIG. 32. The authorized healthcare providers can view the sleep data using a viewer and a viewing application. The viewer and viewing applications can include mobile devices, smartphones, or personal computers with an installed and authorized viewing application.

As shown in FIG. 33, the server 110 can also send commands, configuration data, software updates, and the like (denoted the downstream channel) to the sleep metering system 500 via the network 120 and the wireless hub 610. This downstream channel can be used to specifically configure the operation of a particular sleep metering system 500 based on specific or dynamic conditions, such as providing configuration parameters for a particular sleep metering system 500, configuration for a particular subject, configuration for a particular location or timeframe, configuration for a particular subscription level, a dynamic re-configuration a particular sleep metering system 500 based on a detected set of conditions or events in the particular subject, providing notifications, feedback, instructions, or alerts to the subject, and the like.

Figure 34:
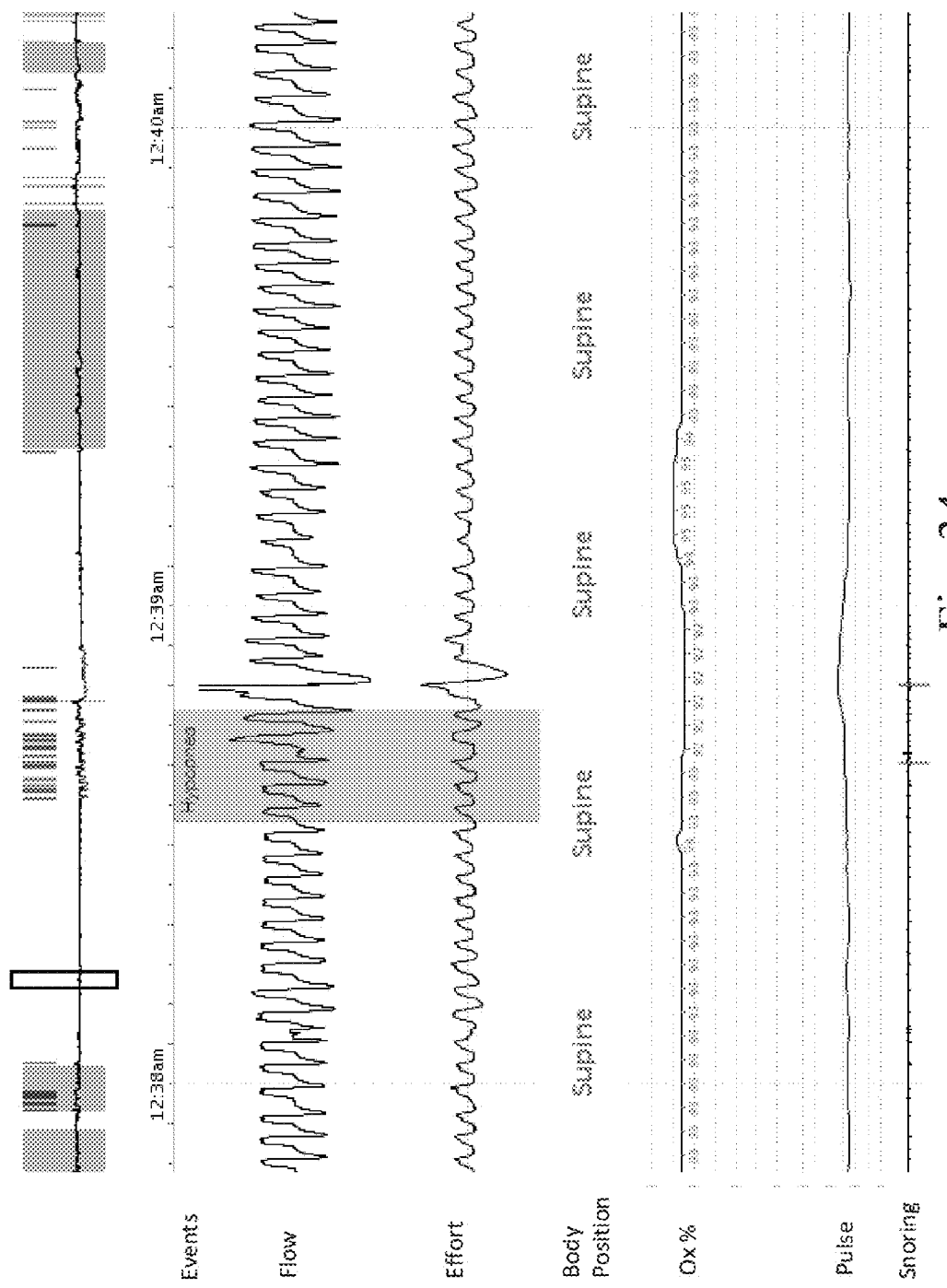
FIG. 34 illustrates an example of scoring a combined set of detected events and conditions in a sleeping subject, the sample scoring indicating a mild Obstructive Sleep Apnea (OSA) condition in the subject based on the detected respiration effort exaggeration event indicated by the airflow and effort channels.

FIG. 34 illustrates an example of scoring a combined set of detected events and conditions in a sleeping subject, the sample scoring indicating a mild Obstructive Sleep Apnea (OSA) condition in the subject based on the detected respiration effort exaggeration event indicated by the airflow and effort channels.

Figure 35:
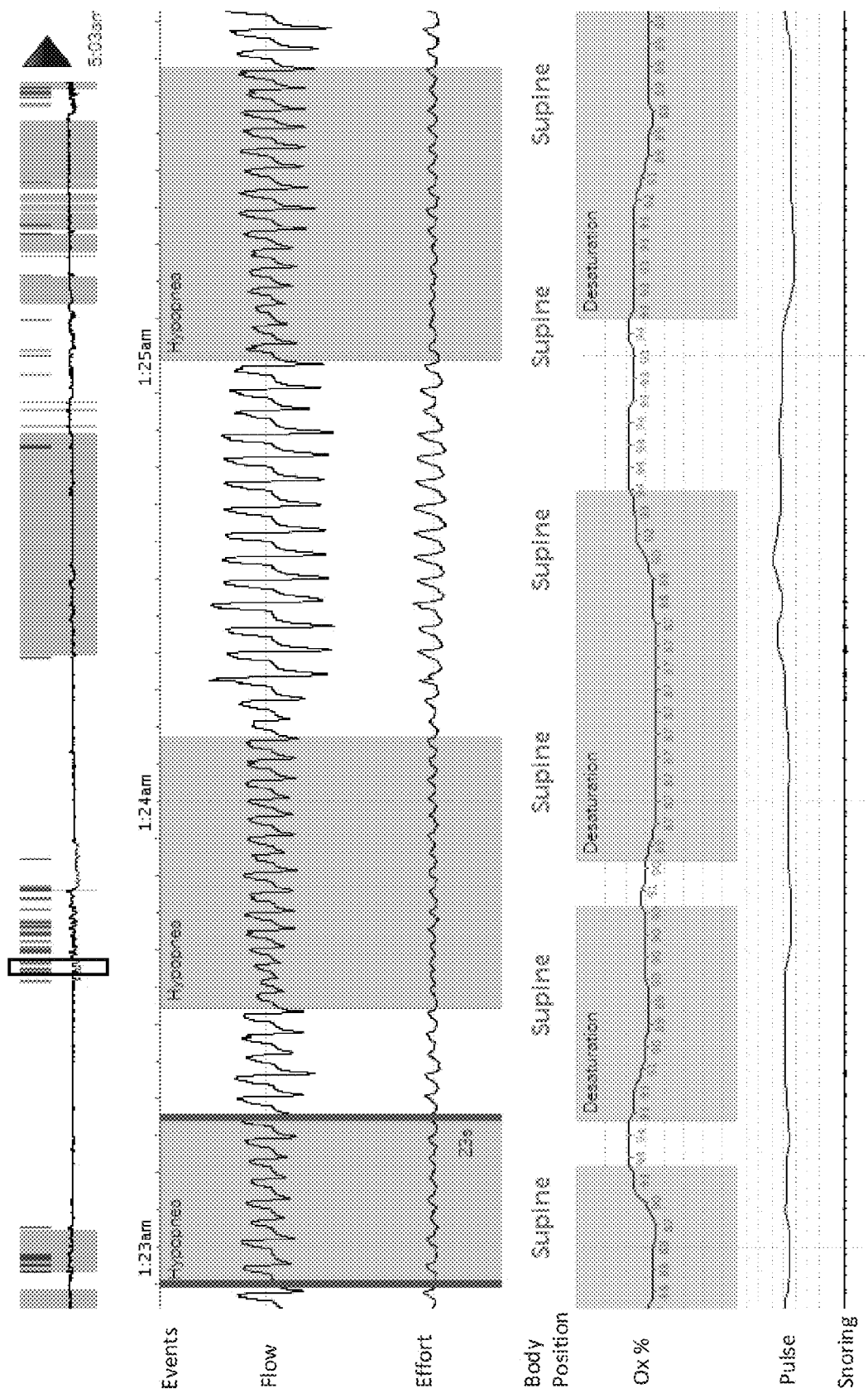
FIG. 35 illustrates an example of scoring a combined set of detected events and conditions in the same sleeping subject, the sample scoring indicating a mild OSA condition in the subject based on the detected respiration effort exaggeration event indicated by the airflow and effort channels, wherein the events are more frequent.

FIG. 35 illustrates an example of scoring a combined set of detected events and conditions in the same sleeping subject, the sample scoring indicating a mild OSA condition in the subject based on the detected respiration effort exaggeration event indicated by the airflow and effort channels, wherein the events are more frequent.

Figure 36:
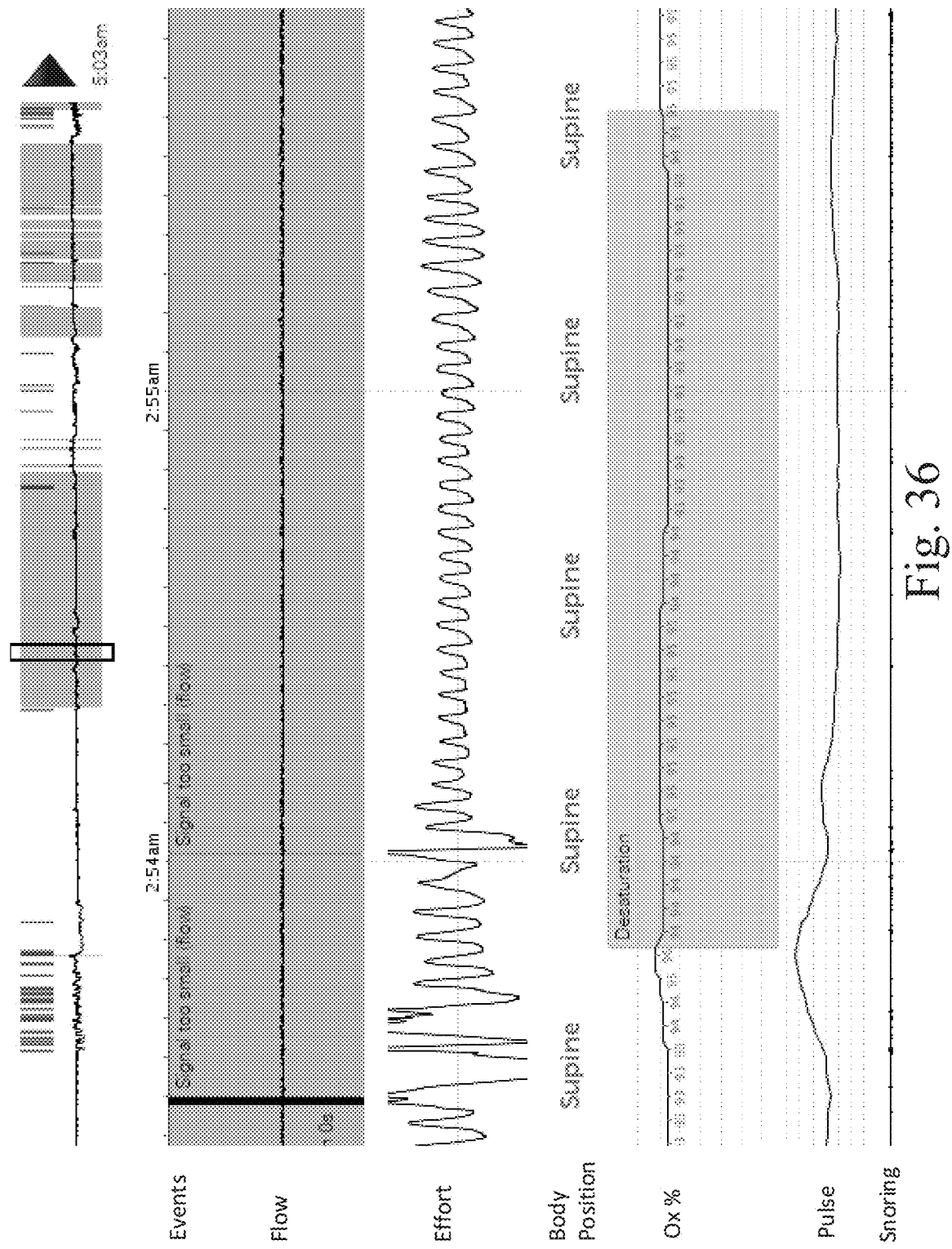
FIG. 36 illustrates an example of scoring a combined set of detected events and conditions in a sleeping subject, the sample scoring indicating an abnormal pattern in the subject based on the detected abdominal channel.

FIG. 36 illustrates an example of scoring a combined set of detected events and conditions in a sleeping subject, the sample scoring indicating an abnormal pattern in the subject based on the detected abdominal channel.

Figure 37:
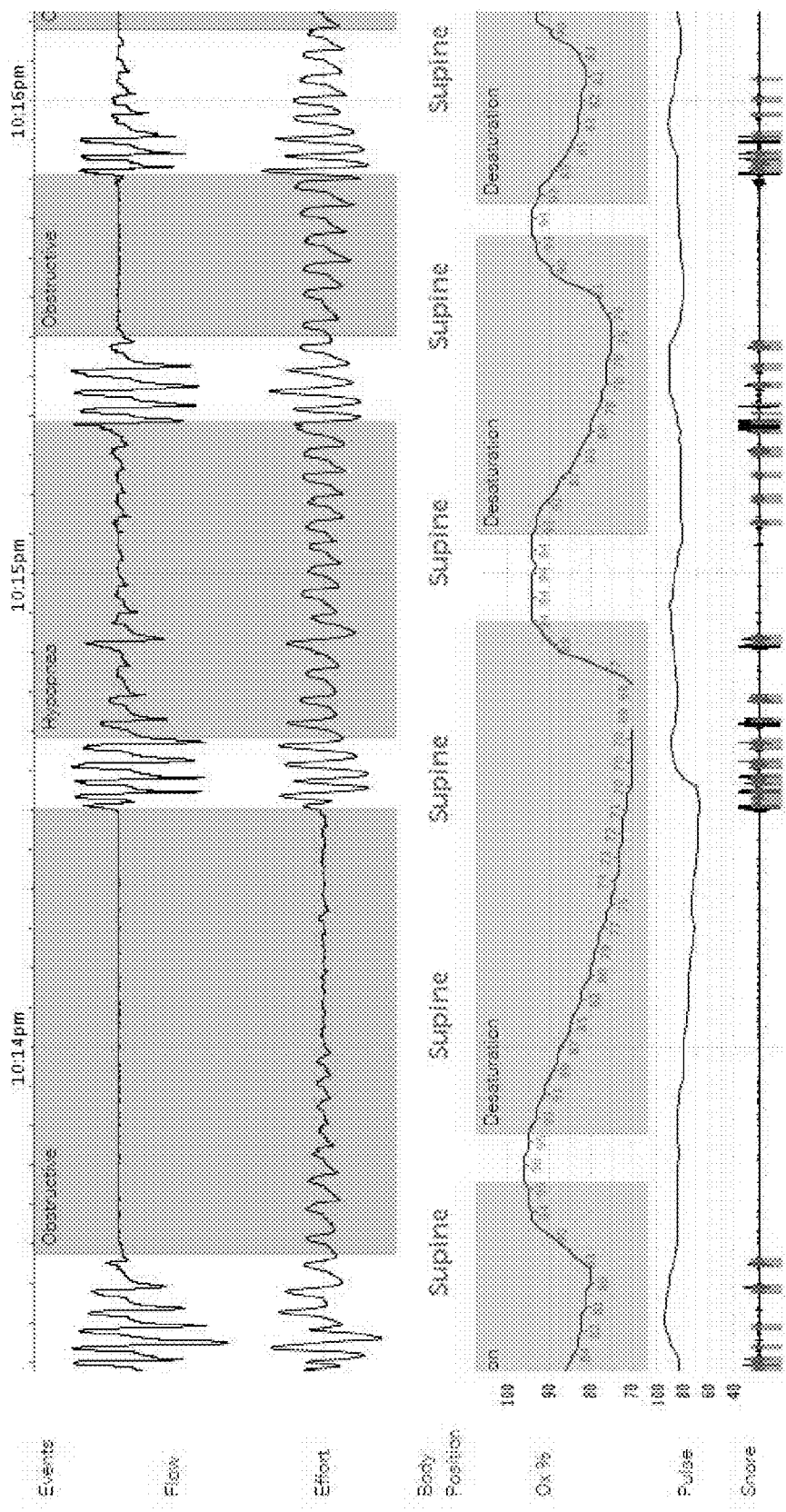
FIG. 37 illustrates an example of scoring a combined set of detected events and conditions in a sleeping subject, the sample scoring indicating a severe OSA condition in the subject based on the redundant pattern detected in all sensor channels.

FIG. 37 illustrates an example of scoring a combined set of detected events and conditions in a sleeping subject, the sample scoring indicating a severe OSA condition in the subject based on the redundant pattern detected in all sensor channels.

Figure 38:
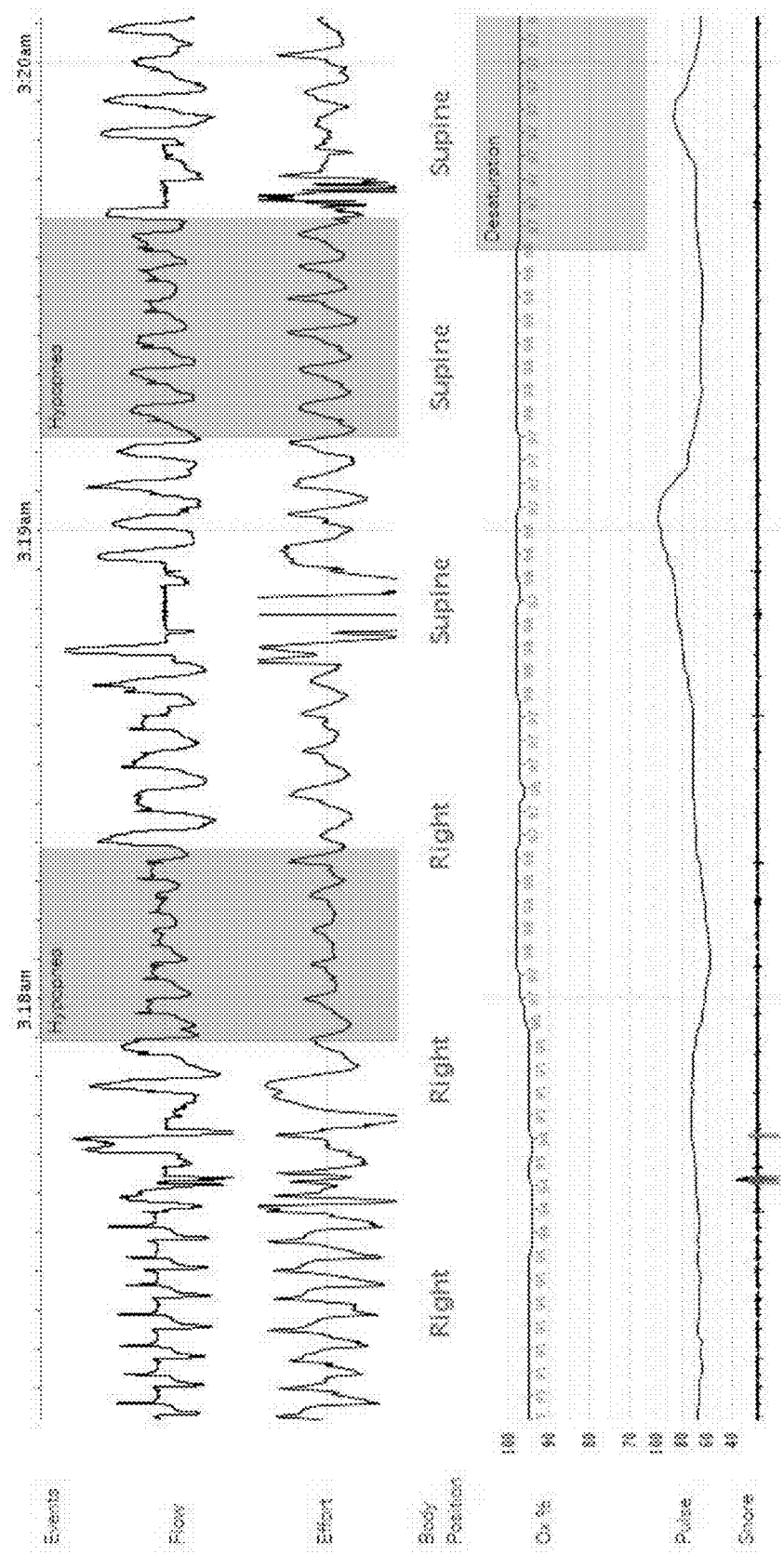
FIG. 38 illustrates an example of scoring a combined set of detected events and conditions in a sleeping subject, the sample scoring indicating a moderate OSA condition in the subject based on a lack of a significant detected snoring condition, but detection of an irregular breathing pattern.

FIG. 38 illustrates an example of scoring a combined set of detected events and conditions in a sleeping subject, the sample scoring indicating a moderate OSA condition in the subject based on a lack of a significant detected snoring condition, but detection of an irregular breathing pattern.

Figure 39:
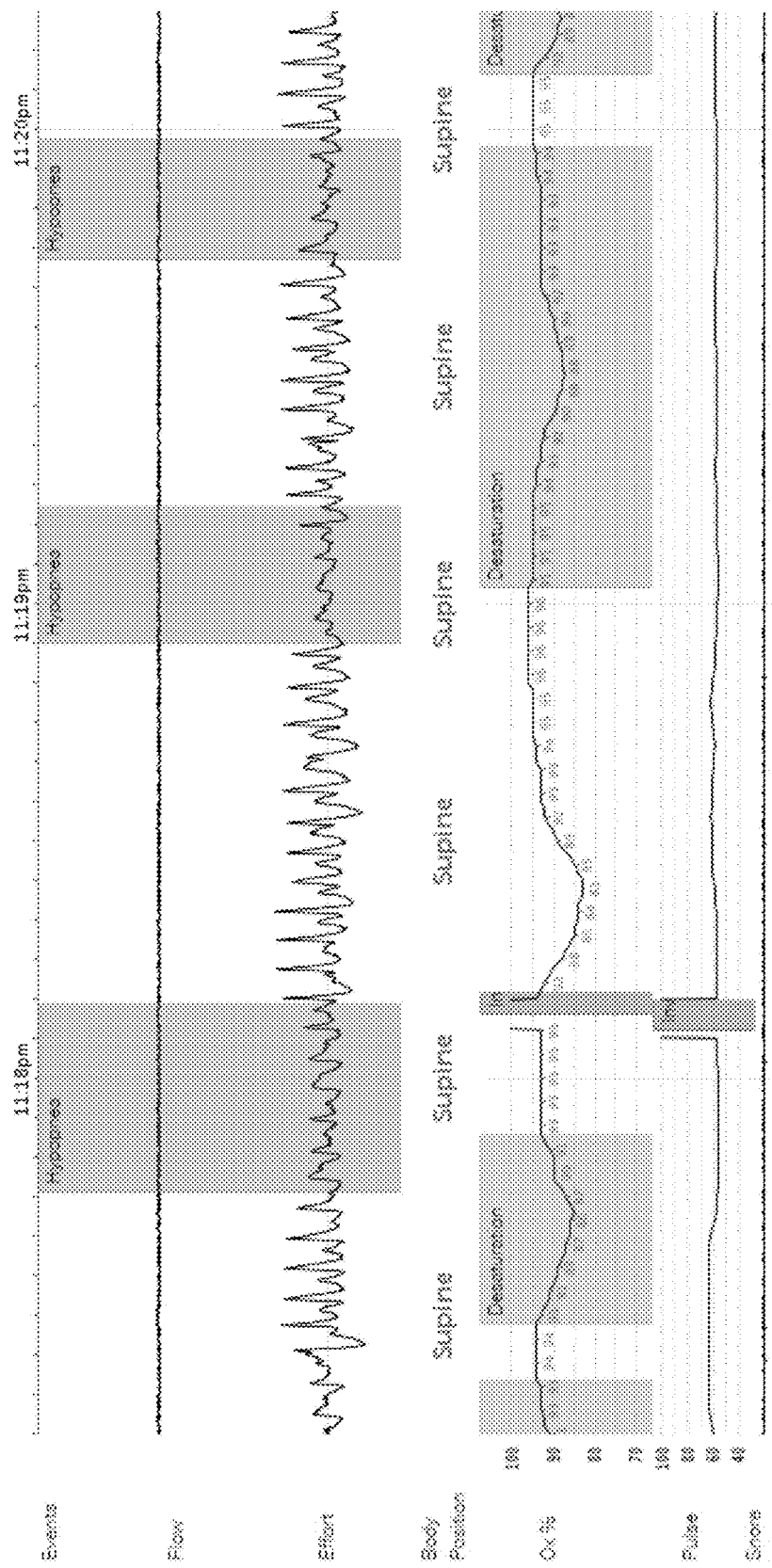
FIG. 39 illustrates an example of scoring a combined set of detected events and conditions in a sleeping subject, the sample scoring indicating a mild OSA condition in the subject based on a lack of detected airflow or snoring conditions, but detection of an abdominal irregular and oxygen desaturations.

FIG. 39 illustrates an example of scoring a combined set of detected events and conditions in a sleeping subject, the sample scoring indicating a mild OSA condition in the subject based on a lack of detected airflow or snoring conditions, but detection of an abdominal irregular and oxygen desaturations.

Figure 40:
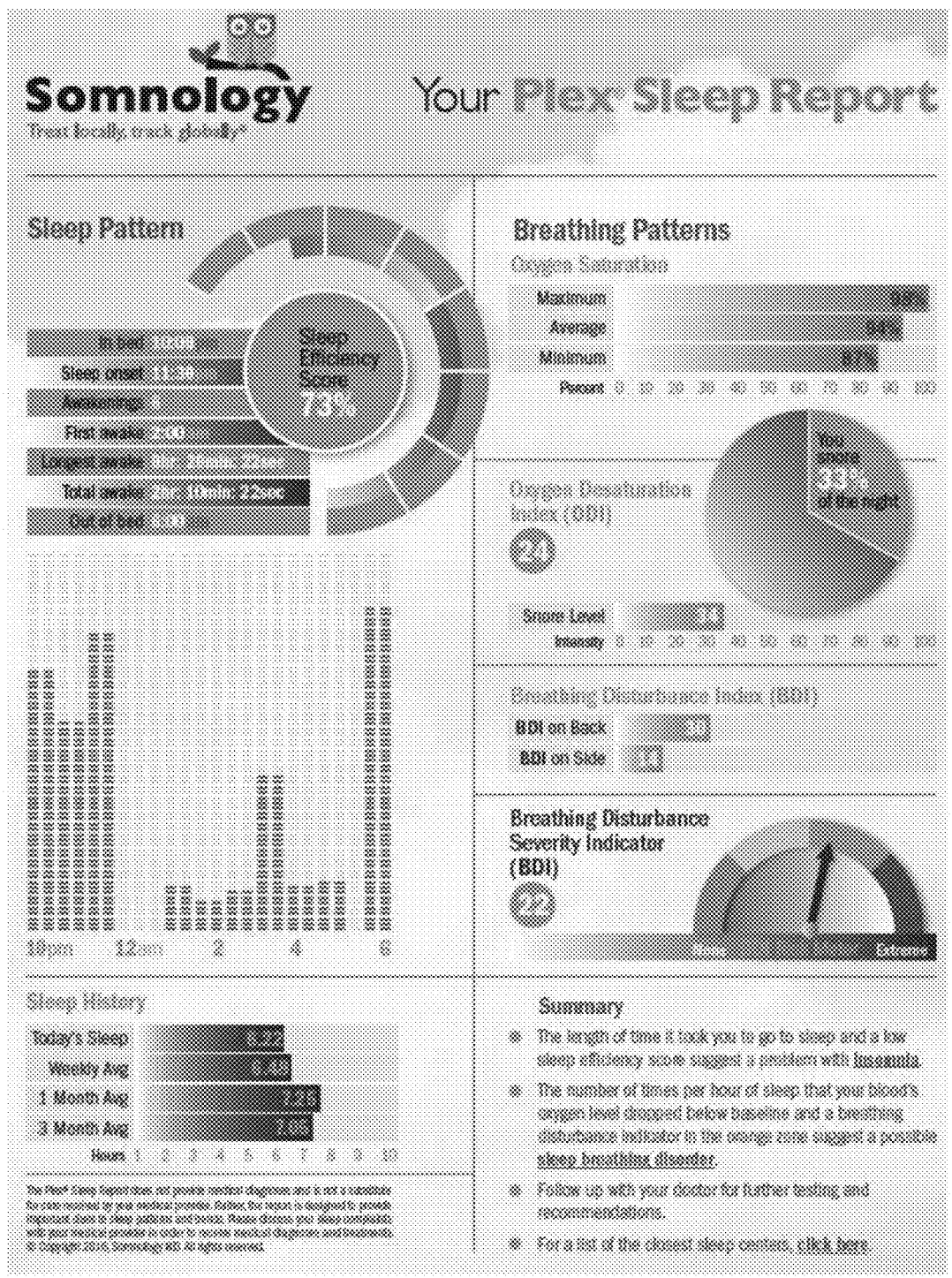
FIG. 40 illustrates an example embodiment of a sleep report containing a variety of information and datasets generated using the sensor data captured and processed for a particular subject by the sleep metering system of an example embodiment.
Figure 41:
FIGS. 41 through 44 illustrate example embodiments of the sleep metering system of an example embodiment.
Figure 42:
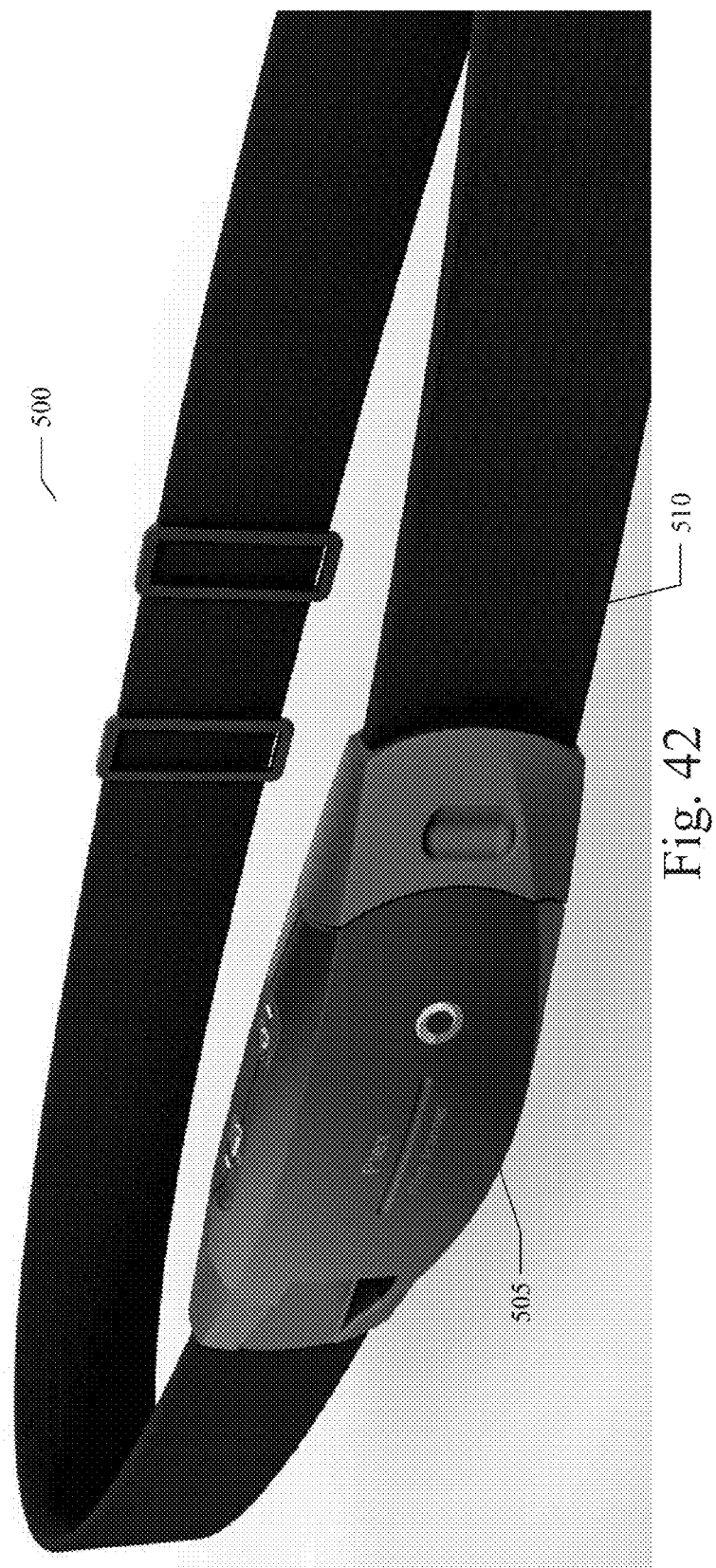
Figure 43:
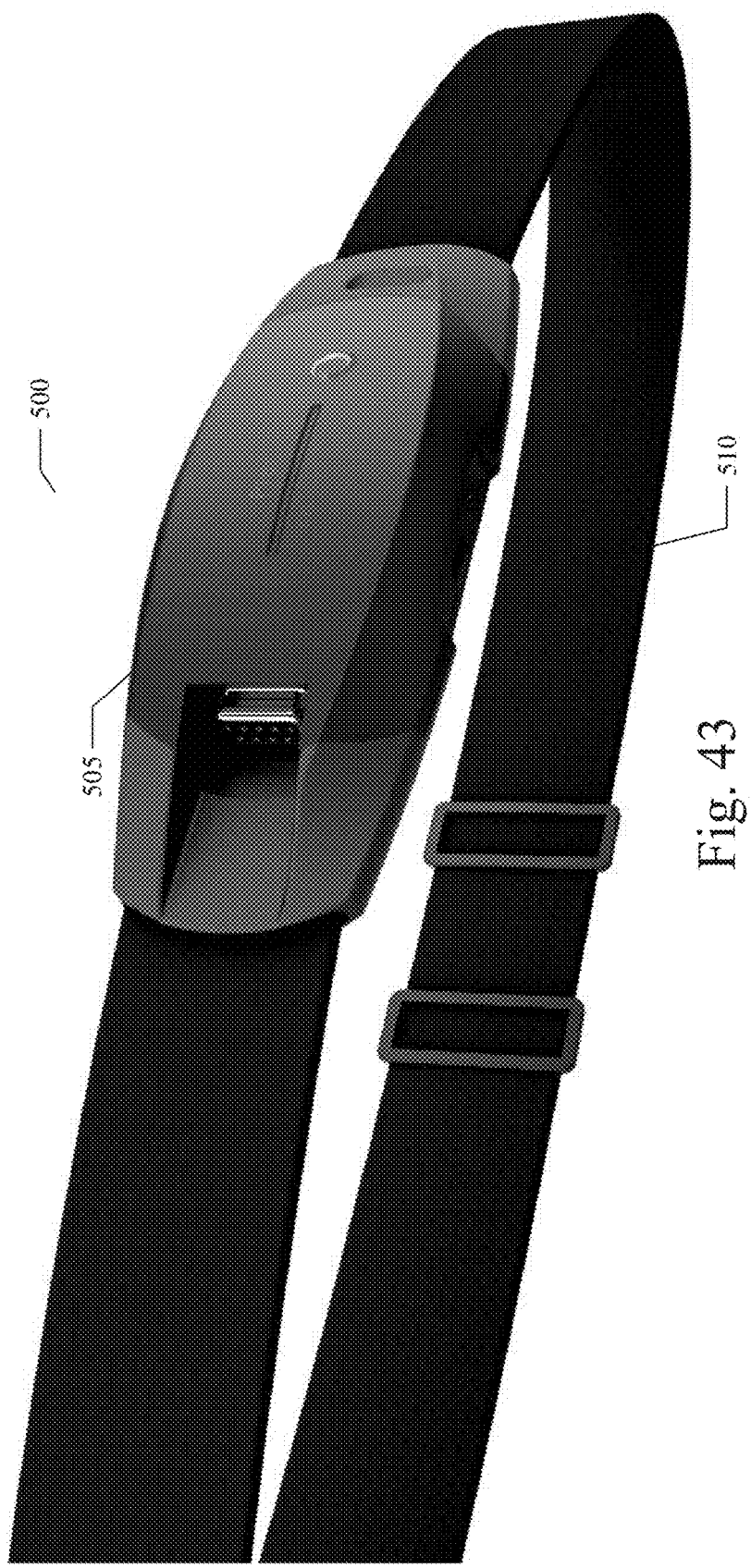
Figure 44:
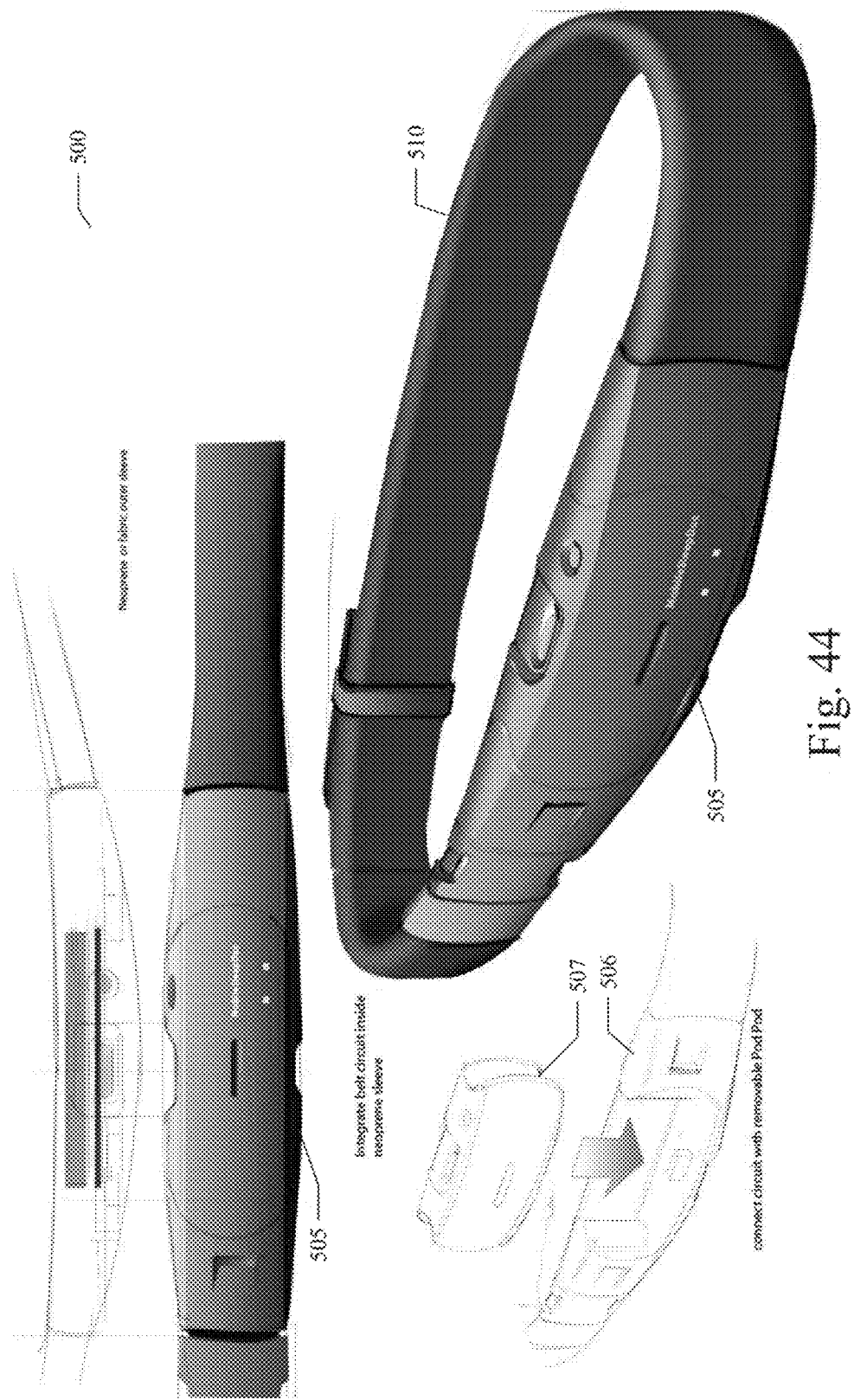

FIG. 40 illustrates an example embodiment of a sleep report containing a variety of information and datasets generated using the sensor data captured and processed for a particular subject by the sleep metering system of an example embodiment. For example, the sample sleep report shows information datasets including: the sleep efficiency score for a particular subject as generated by the sleep disorder diagnosis and treatment system of an example embodiment, the particular subject's breathing patterns over the test period, the subject's oxygen desaturation index, BDI, a BDI severity indication, a sleep history, and a summary of the subject's sleep analysis and diagnosis. Each of the information datasets are based on actual sensor data retrieved from the subject as the subject was wearing the sleep metering system 500 over a test period. As such, the information datasets generated by the sleep disorder diagnosis and treatment system of an example embodiment are based on the capture and processing of physical data signals representing a physical state or condition of a human subject.

The example embodiments described herein provide a technical solution to a technical problem. The various embodiments improve the functioning of the electronic devices and the related system by providing a system and method for sleep disorder diagnosis and treatment of a particular human subject. The various embodiments also serve to transform the state of various system components based on a dynamically determined system context and the state of the subject being analyzed. Additionally, the various embodiments effect an improvement in a variety of technical fields including the fields of dynamic data and signal processing, electronic systems, mobile devices, wearable devices, data sensing systems, human/machine interfaces, mobile computing, information sharing, and mobile communications.

FIGS. 41 through 44 illustrate example embodiments of the sleep metering system of an example embodiment. In particular, FIGS. 41 through 44 shown an example embodiment including a housing 505 containing an array of sensors for detecting various conditions and events in a human subject wearing the sleep metering system 500 around their chest. The housing 505 is configured in an elongated low profile design to minimize the discomfort of a subject wearing the sleep metering system 500 during sleep. A belt or strap 510 is coupled to the housing 505 in a loop to enable the sleep metering system 500 to be attached to the chest of a subject while the subject is sleeping. In an embodiment shown in FIG. 44, the housing 505 can include a removable portion 507 that can be snapped into and out of an attached portion 506. The removable portion 507 enables a user to readily replace the main components of the sleep metering system 500 to provide additional functionality, replace a defective unit, or upgrade the system.

The various elements of the example embodiments as previously described with reference to the figures may include various hardware elements, software elements, or a combination of both. Examples of hardware elements may include devices, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. However, determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A computer-implemented method for improving detection of sleep-related conditions, the method comprising:
   establishing, by use of a data processor, a wireless data communication interface between the data processor and a sleep metering system worn by a user, the sleep metering system including a sensor array, wireless transceiver, and a processor;
   positioning the sleep metering system for data recording externally at the top of the user's abdomen, the sleep metering system being removably attached to the user with an inductive belt being a chest expansion and respiratory effort measuring device to detect and measure airflow and respiratory effort in the user;
   collecting, by use of the sleep metering system, sensor data from the user based on data signals from the sensor array of the sleep metering system;
   receiving, by use of the data processor, a single abdominal effort channel waveform based on the collected sensor data from the sleep metering system, the single abdominal effort channel waveform representing breathing pattern data corresponding to variations in the degree of the user's abdominal effort in a series of breaths over a given time interval;
   detecting, by use of the data processor, a sleep-related condition in the user by use of the breathing pattern data from the sleep metering system, the sleep-related condition including anomalies in breathing patterns of the user based on the breathing pattern data from the sleep metering system at a plurality of pre-defined time intervals within a single sleep period;
   identifying, by use of the data processor, a respiratory effort reduction or exaggeration condition for a level of severity over the plurality of pre-defined time intervals using the breathing pattern data from the sleep metering system and the detected sleep-related condition; and
   performing a dynamic re-configuration of the sleep metering system based on the detected sleep-related condition.

2. The method of claim 1 including generating a user interface as a web application.

3. The method of claim 1 including generating a user interface as a mobile application.

4. The method of claim 1 including generating a value on an Epworth Sleepiness Scale (ESS).

5. The method of claim 1 including generating a sleep report containing information and datasets generated using the sensor data captured and processed for the user.

6. The method of claim 1 including generating a sleep log including information indicative of the time when the user got into bed, the time when the user got out of bed, the time when the user actually fell asleep, and the time when the user woke up.

7. The method of claim 1 wherein the sensor array includes sensors of a type from the group consisting of: a motion detection device, a sound detection device, a pulse oximeter device, and a respiratory effort detection device.

8. The method of claim 1 including generating a sleep efficiency score based on the sensor data captured and processed for the user.

9. The method of claim 1 including attaching the sleep metering system at the top of the user's abdomen with a strap.

10. A system for improving detection of sleep-related conditions, the system comprising:
   a networked data processor;
   a memory, in data communication with the networked data processor;
   a sleep metering system in wireless data communication with the networked data processor, the sleep metering system being worn by the user and including a sensor array, wireless transceiver, and a processor, the sleep metering system being positioned for data recording externally at the top of the user's abdomen, the sleep metering system being removably attached to the user with an inductive belt being a chest expansion and respiratory effort measuring device to detect and measure airflow and respiratory effort in the user; and
   a sleep disorder diagnosis and treatment system, executable by the networked data processor, to:
      establish a wireless data communication interface between the networked data processor and the sleep metering system;
      activate the sleep metering system to collect sensor data from the user based on data signals from the sensor array of the sleep metering system;
      receive, at the networked data processor, a single abdominal effort channel waveform based on the collected sensor data from the sleep metering system, the single abdominal effort channel waveform representing breathing pattern data corresponding to variations in the degree of the user's abdominal effort in a series of breaths over a given time interval;
detect a sleep-related condition in the user by use of the breathing pattern data from the sleep metering system, the sleep-related condition including anomalies in breathing patterns of the user based on the breathing pattern data from the sleep metering system at a plurality of pre-defined time intervals within a single sleep period;
identify, by use of the networked data processor, a respiratory effort reduction or exaggeration condition for a level of severity over the plurality of pre-defined time intervals using the breathing pattern data from the sleep metering system and the detected sleep-related condition; and
perform a dynamic re-configuration of the sleep metering system based on the detected sleep-related condition.

11. The system of claim 10 being further configured to generate a user interface as a web application.

12. The system of claim 10 being further configured to generate a user interface as a mobile application.

13. The system of claim 10 being further configured to generate a value on an Epworth Sleepiness Scale (ESS).

14. The system of claim 10 being further configured to generate a sleep report containing information and datasets generated using the sensor data captured and processed for the user.

15. The system of claim 10 being further configured to generate a sleep log including information indicative of the time when the user got into bed, the time when the user got out of bed, the time when the user actually fell asleep, and the time when the user woke up.

16. The system of claim 10 wherein the sensor array includes sensors of a type from the group consisting of: a motion detection device, a sound detection device, a pulse oximeter device, and a respiratory effort detection device.

17. The system of claim 10 being further configured to generate a sleep efficiency score based on the sensor data captured and processed for the user.

18. The system of claim 10 including the sleep metering system being attached at the top of the user's abdomen with a strap.

19. A non-transitory machine-useable storage medium embodying instructions which, when executed by a machine, cause the machine to:
establish a wireless data communication interface between a networked data processor and a sleep metering system, the sleep metering system being worn by a user and including a sensor array, wireless transceiver, and a processor, the sleep metering system being positioned for data recording externally at the top of the user's abdomen, the sleep metering system being removably attached to the user with an inductive belt being a chest expansion and respiratory effort measuring device to detect and measure airflow and respiratory effort in the user;
activate the sleep metering system to collect sensor data from the user based on data signals from the sensor array of the sleep metering system;
receive, at the networked data processor, a single abdominal effort channel waveform based on the collected sensor data from the sleep metering system, the single abdominal effort channel waveform representing breathing pattern data corresponding to variations in the degree of the user's abdominal effort in a series of breaths over a given time interval;
detect a sleep-related condition in the user by use of the breathing pattern data from the sleep metering system, the sleep-related condition including anomalies in breathing patterns of the user based on the breathing pattern data from the sleep metering system at a plurality of pre-defined time intervals within a single sleep period;
identify a respiratory effort reduction or exaggeration condition for a level of severity over the plurality of pre-defined time intervals using the breathing pattern data from the sleep metering system and the detected sleep-related condition; and
perform a dynamic re-configuration of the sleep metering system based on the detected sleep-related condition.

20. The machine-useable storage medium of claim 19 wherein the sensor array includes sensors of a type from the group consisting of: a motion detection device, a sound detection device, a pulse oximeter device, and a respiratory effort detection device.

* * * * *